US010292779B2

(12) United States Patent
Farahmand et al.

(10) Patent No.: US 10,292,779 B2
(45) Date of Patent: May 21, 2019

(54) ADAPTING MANUAL LAPAROSCOPIC SURGICAL INSTRUMENTS FOR ROBOTIC TELESURGERY APPLICATIONS

(71) Applicant: SINA ROBOTICS AND MEDICAL INNOVATORS CO., Tehran OT (IR)

(72) Inventors: Farzam Farahmand, Tehran (IR); Alireza Mirbagheri, Tehran (IR); Saeed Behzadipour, Tehran (IR); Alireza Alamdar, Tehran (IR); Shahrzad Hanifeh, Tehran (IR); Seyed Mohsen Khadem, Edmonton (CA); Mohamad Mehdi Moradi, Tehran (IR)

(73) Assignee: SINA ROBOTICS AND MEDICAL INNOVATORS CO., Tehran (IR)

( * ) Notice: Subject to any disclaimer, the term of this patent is extended or adjusted under 35 U.S.C. 154(b) by 206 days.

(21) Appl. No.: 15/151,869

(22) Filed: May 11, 2016

(65) Prior Publication Data
US 2016/0249993 A1    Sep. 1, 2016

Related U.S. Application Data

(60) Provisional application No. 62/258,588, filed on Nov. 23, 2015.

(51) Int. Cl.
| A61B 17/00 | (2006.01) |
| A61B 34/30 | (2016.01) |
| A61B 34/35 | (2016.01) |
| A61B 34/00 | (2016.01) |

(52) U.S. Cl.
CPC ............ *A61B 34/35* (2016.02); *A61B 34/71* (2016.02); *A61B 34/76* (2016.02); *A61B 2017/00486* (2013.01); *A61B 2034/305* (2016.02)

(58) Field of Classification Search
CPC .......... A61B 1/00133; A61B 2034/301; A61B 2034/305; A61B 34/32; A61B 34/35; A61B 34/37; A61B 34/71; A61B 2017/00464; A61B 2017/0046; A61B 2017/00486
USPC ..... 227/141; 74/490.05, 490.06; 901/15, 18, 901/28, 29
See application file for complete search history.

(56) References Cited

U.S. PATENT DOCUMENTS

| 4,863,133 | A  | * | 9/1989  | Bonnell   | F16M 11/14  |
|           |    |   |         |           | 248/280.11  |
| 5,623,582 | A  | * | 4/1997  | Rosenberg | B25J 9/1689 |
|           |    |   |         |           | 700/264     |
| 6,325,808 | B1 | * | 12/2001 | Bernard   | A61B 17/0469|
|           |    |   |         |           | 318/568.11  |
| 8,231,610 | B2 | * | 7/2012  | Jo        | A61B 34/70  |
|           |    |   |         |           | 600/429     |
| 8,282,653 | B2 | * | 10/2012 | Nelson    | A61B 34/30  |
|           |    |   |         |           | 600/417     |

(Continued)

FOREIGN PATENT DOCUMENTS

CN           102029614       *  5/2012  ............. B25J 17/02

*Primary Examiner* — Howard J Sanders
*Assistant Examiner* — Bobby Rushing, Jr.
(74) *Attorney, Agent, or Firm* — NovoTechIP International PLLC

(57) ABSTRACT

A tool adapting device attaches to a robotic surgery arm, and receives a manual surgical instrument, and translates movement by the robotic surgery arm into multiple degrees of freedom of the manual surgical instrument, to interact with a tissue under surgery.

14 Claims, 18 Drawing Sheets

(56) References Cited

U.S. PATENT DOCUMENTS

| | | | |
|---|---|---|---|
| 8,764,448 B2* | 7/2014 | Yang | G09B 23/28 |
| | | | 434/262 |
| 2003/0115954 A1* | 6/2003 | Zemlyakov | A61B 5/022 |
| | | | 73/379.01 |
| 2006/0195070 A1 | 8/2006 | Hagn | |
| 2009/0024142 A1 | 1/2009 | Ruiz Morales | |
| 2012/0245596 A1 | 9/2012 | Meenink | |
| 2013/0060278 A1* | 3/2013 | Bozung | A61B 17/32002 |
| | | | 606/205 |
| 2014/0039314 A1* | 2/2014 | Stoianovici | A61B 8/0841 |
| | | | 600/439 |
| 2014/0222023 A1* | 8/2014 | Kim | A61B 19/2203 |
| | | | 606/130 |

* cited by examiner

ADAPTING MANUAL LAPAROSCOPIC SURGICAL INSTRUMENTS FOR ROBOTIC TELESURGERY APPLICATIONS

CROSS REFERENCE TO RELATED APPLICATION

This application claims the benefit of priority from U.S. Provisional Patent Application Ser. No. 62/258,588, filed on Nov. 23, 2015, and entitled "USING HAND-HELD LAPAROSCOPIC SURGICAL TOOLS IN ROBOTIC TELESURGERY SYSTEMS," which is incorporated by reference herein in its entirety.

TECHNICAL FIELD

The present application generally relates to robotic tele-surgery systems, particularly to assemblies attached to the robotic tele-surgery systems for gripping and activating laparoscopic tools, and more particularly to a tool adapting device that facilitates connection and manipulation of manual laparoscopic tools on an arm of a robotic tele-surgery system.

BACKGROUND

The robotic tele-surgery systems enable performing remote surgery operations with minimal invasion. These systems include master and slave robots. The master robot works as the interface between the surgeon and the slave robots. The surgeon operates and controls the slave robots using the master robot, while sitting or standing in an ergonomic position. The master robot receives the surgeon's commands and movements, scales them and removes tremor, and transfers them to the slave robot to be applied to the surgery site. As a result, the surgery may be performed with higher accuracy and less trauma to the patient. In fact, the robotic tele-surgery systems enable combining the human knowledge and decision making abilities with the advanced technical features of robotics to provide the capability of performing remote surgery, as well as improving the outcomes of the surgery by enhancing the surgeon's dexterity.

The slave robots that are located at the patient side include a number of surgical and endoscopic robotic arms that are controlled by the surgeon. The robotic surgical arms have several degrees of freedom to provide sufficient work-space and maneuverability for surgery. They are usually integrated with special surgical instruments at their end-effectors to interact with the tissues under surgery. The use of integrated and exclusively designed surgical instruments increases the costs of surgical operations using robotic tele-surgery systems. The high costs of using the existing robotic tele-surgery systems are mainly due to the costly maintenance and the demand for using single- or limited-use robotic appliances.

Therefore, it would be desirable to provide improved robotic tele-surgery systems, methods and techniques to allow easy replacement of the single- or limited-use components to reduce the maintenance costs. It would be further desirable to provide designs and methodologies that can make the robotic tele-surgery systems capable of working with non-exclusively designed surgical instruments that are widely accessible at lower prices. Therefore, there is a need in the art for a tool adapting device that can facilitate the connection and manipulation of relatively inexpensive manual laparoscopic surgical instruments on a robotic surgery arm.

SUMMARY

The following brief summary is not intended to include all features and aspects of the present application, nor does it imply that the application must include all features and aspects discussed in this summary.

In one general aspect, the instant application describes a tool adapting device for adapting manual surgical instruments for robotic surgery applications including: an attachment interface, which is configured for connecting the tool adapting device to a distal end of a robotic surgery arm; and a tool activating mechanism, which is configured for holding a manual surgical instrument and activating degrees of freedom of the manual surgical instrument to interact with a tissue under surgery. In an aspect, the tool activating mechanism can be controllable via the robotic surgery arm.

In another general aspect, a method is described for adapting manual surgical instruments for robotic surgery applications, including steps of: attaching a tool adapting device on the distal end of the robotic surgery arm; and placing a manual laparoscopic surgical tool inside the tool adapting device. In an aspect, the tool adapting device can activate the degrees of freedom of the manual laparoscopic surgical instrument to interact with a tissue under surgery.

The above general aspects may include one or more of the following features. The manual surgical instrument can be selected from a group consisting of non-articulating laparoscopic instruments, handled wrist-articulating instruments and handle-free wrist articulating instruments, and any sub-combination or combination thereof. The degrees of freedom of the manual surgical instrument can include grasp, roll, pitch, and yaw.

According to some implementations, the tool activating mechanism can include: a first actuating mechanism for activating a grasp degree of freedom of the manual surgical instrument, where the manual surgical instrument has an actuating cable movable inside a sleeve and an end-effector. The first actuating mechanism can be configured to move the actuating cable of the manual surgical instrument in a linear axial movement inside the sleeve along a longitudinal axis of the sleeve, and consequently activate the grasp degree of freedom of the end-effector; and a second actuating mechanism for activating a roll degree of freedom of the manual surgical instrument, where the second actuating mechanism can be configured to rotate the sleeve about the longitudinal axis of the sleeve, and consequently activate the roll degree of freedom of the end-effector.

According to other implementations, the tool activating mechanism can further include a third actuating mechanism for activating pitch and yaw degrees of freedom of the manual surgical instrument, where the manual surgical instrument has a wrist joint configured for activating the pitch and yaw degrees of freedom of the end-effector. The third actuating mechanism is configured to rotate the wrist joint of the manual surgical instrument about pitch and yaw axes and activate the pitch and yaw degrees of freedom of the end-effector.

According to an implementation, the first actuating mechanism can include a linear actuating mechanism coupled with the actuating cable of the manual surgical instrument and configured to move the actuating cable of the manual surgical instrument in a linear axial movement inside the sleeve along a longitudinal axis of the sleeve, thereby activating the grasp degree of freedom of the end-effector. The linear actuating mechanism can be selected from a group consisting of ball screw mechanisms, nut screw mechanisms, and electromagnetic linear actuators, rack-and-pinion mechanisms, cable mechanisms, and electrical jacks, pneumatic or hydraulic jacks. According to another implementation, the linear actuating mechanism can include a rotational actuator coupled with a ball screw assembly.

According to an implementation, the second actuating mechanism can include a rotational actuating mechanism coupled with the sleeve of the manual surgical instrument and configured to rotate the sleeve about the longitudinal axis of the sleeve, thereby activating the roll degree of freedom of the end-effector. The rotational actuating mechanism can be coupled with the sleeve of the surgical instrument via a coupling mechanism selected from a group consisting of gear mechanisms, chain-wheel mechanism, or belt-and-pulley mechanisms. According to another implementation, the rotational actuating mechanism can be coupled with the sleeve of the surgical instrument via a belt-and-pulley coupling mechanism.

According to one implementation, the third actuating mechanism can include an actuating mechanism coupled with a spherical mechanism attached to a handle of the manual surgery instrument, and the actuating mechanism can be configured to rotate the handle of the manual surgery instrument about pitch and yaw axes relative to the sleeve of the manual surgical instrument via the spherical mechanism, thereby activating the pitch and yaw degrees of freedom of the end-effector. The actuating mechanism can include two rotational actuators.

According to another implementation, the third actuating mechanism can include an actuating mechanism coupled with a parallel mechanism attached to the wrist joint of the manual surgery instrument, and the actuating mechanism can be configured to rotate the wrist joint of the manual surgery instrument about pitch and yaw axes via the parallel mechanism, thereby activating the pitch and yaw degrees of freedom of the end-effector.

According to some implementations, the tool activating mechanism can further include a force sensor, configured to send a grasp force feedback to the surgeon.

BRIEF DESCRIPTION OF THE DRAWINGS

While the specification concludes with claims particularly pointing out and distinctly claiming the subject matter that is regarded as forming the present application, it is believed that the application will be better understood from the following description taken in conjunction with the accompanying DRAWINGS, where like reference numerals designate like structural and other elements, in which:

DETAILED DESCRIPTION

Figure 1A:
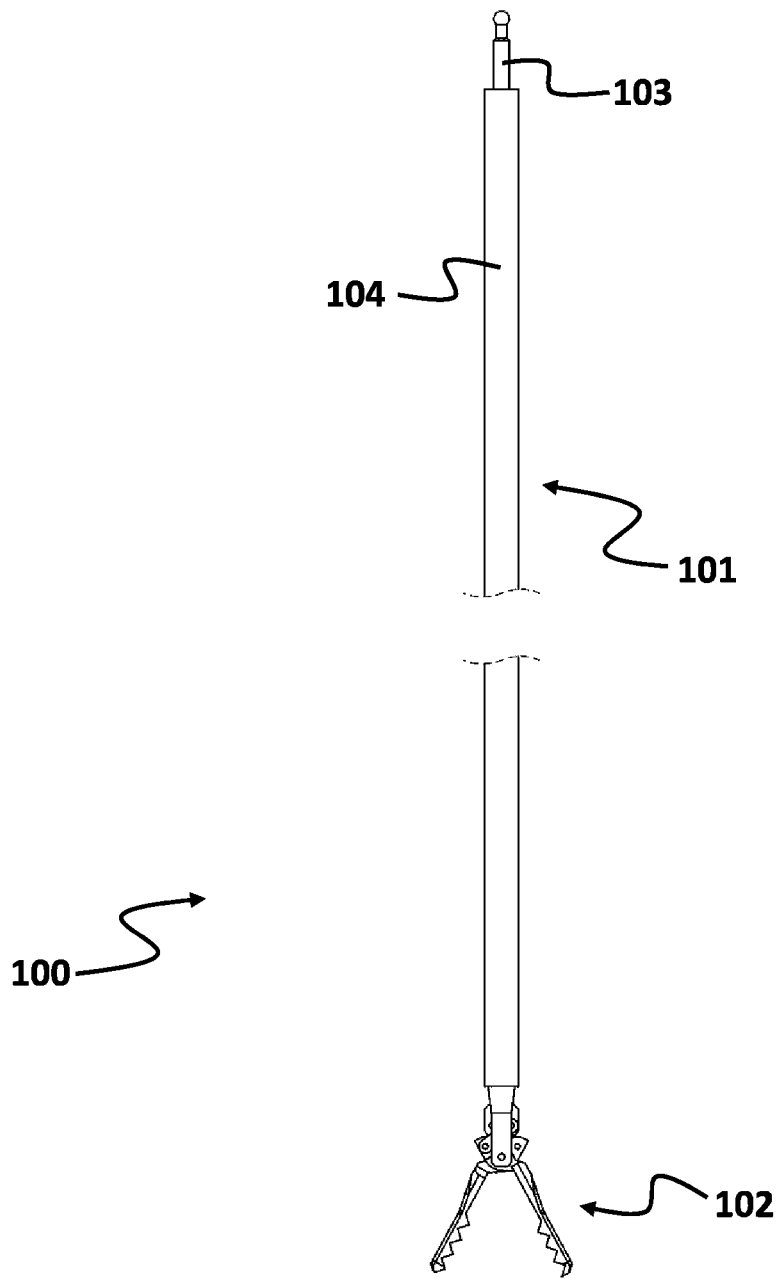
FIG. 1A illustrates an exemplar simple non-articulating laparoscopic surgical instrument.

In the following detailed description, numerous specific details are set forth by way of examples in order to provide a thorough understanding of various features, concepts and aspects thereof However, it should be apparent that the present teachings may be practiced without such details. In other instances, well known methods, procedures, components, and/or circuitry have been described at a relatively high-level, without detail, in order to avoid unnecessarily obscuring aspects of the present teachings.

For purposes of explanation, specific nomenclature is set forth to provide a thorough understanding of the present application. However, it will be apparent to one skilled in the art that these specific details are not required to practice the application. Descriptions of specific applications are provided only as representative examples. Upon reading the present disclosure in its entirety, various modifications to the example implementations that do not depart from the scope of the application may become apparent to one skilled in the art. In addition, upon reading the present disclosure in its entirety, such persons may see that various disclosed concepts, principles and aspects thereof may be applied to other implementations and applications without departing from the scope of the disclosed concepts, principles and aspects thereof. The present application is not intended to be limited to the implementations shown, but is to be accorded the widest possible scope consistent with the principles and features disclosed herein.

Described in this application is a tool adapting device for connecting and manipulating manual surgical instruments on a robotic surgical system. The tool adapting device can include: an attachment interface, for connecting the tool adapting device to a distal end of an arm of the robotic surgical system; and a tool activating mechanism configured for manipulating the manual surgical instruments to interact with the tissues under surgery. The manual surgical instruments can include, for example manual laparoscopic instruments. The tool activating mechanism can be controllable via the robotic surgical system.

As used in this application, the term "manipulating a manual surgical instrument means activating degrees of freedom (DOFs) of the manual surgical instrument. The term "manual laparoscopic surgical instruments" can encompass, for example, and without limitation, simple non-articulating surgical instruments and wrist-articulating surgical instruments. The manual laparoscopic surgical instruments can have up to four DOFs, including: grasp, roll, pitch, and yaw.

The attachment interface of the tool adapting device can facilitate a firm fixation of the tool adapting device to the distal end of the arm of the robotic surgical system. The design of the attachment interface can be adaptable and depend upon the design characteristics of the robotic surgical arm.

The tool activating mechanism of the tool adapting device can be configured for activating DOFs of different types of manual laparoscopic surgical instruments. The tool activating mechanism can include servo-mechanical assemblies that grip, and hold proximal end and/or middle portions of laparoscopic surgical instruments and engage knobs, buttons, levers, slides and other control mechanisms of the manual laparoscopic surgical instruments and provide full control over DOFs of the instrument. The design of the tool activating mechanism can be adaptable and depend on the design and functional characteristics of the manual laparoscopic surgical instruments.

FIG. 1A illustrates an exemplar simple non-articulating laparoscopic surgical instrument 100 having two DOFs of grasp and roll. The surgical instrument 100 can include a shaft 101 and an end-effector 102. The shaft 101 can include an actuating cable (or rod) 103 movable inside a sleeve 104. The sleeve 104 can be configured to facilitate a linear sliding movement of the actuating cable (or rod) 103 along the longitudinal axis of the shaft 101. The actuating cable (or rod) 103 can be operably connected to the end-effector 102 such that the linear sliding movement of the actuating cable (or rod) 103 activates the grasp degree of freedom (DOF) of the end-effector 102. Moreover, a roll-rotation of the shaft 101 can lead to a roll-rotation of the end-effector 102 about the longitudinal axis of the end-effector 102. The simple non-articulating laparoscopic surgical instruments can utilize a handle assembly (not shown in FIG. 1A) to facilitate linear actuation of the actuating cable (or rod) 103. The handle assembly can be configured with different configurations, including, for example, pistol-type configurations or scissor-type configurations. In the pistol-type configurations a trigger can be coupled with the actuating cable (or rod) 103, which functions to linearly pull the actuating cable (or rod) 103 in an axial linear movement inside the sleeve 104. In the scissor-type configurations a movable handle can be coupled with the actuating cable (or rod) 103, which functions to linearly pull the actuating cable (or rod) 103 in an axial linear movement inside the sleeve 104.

Figure 1B:
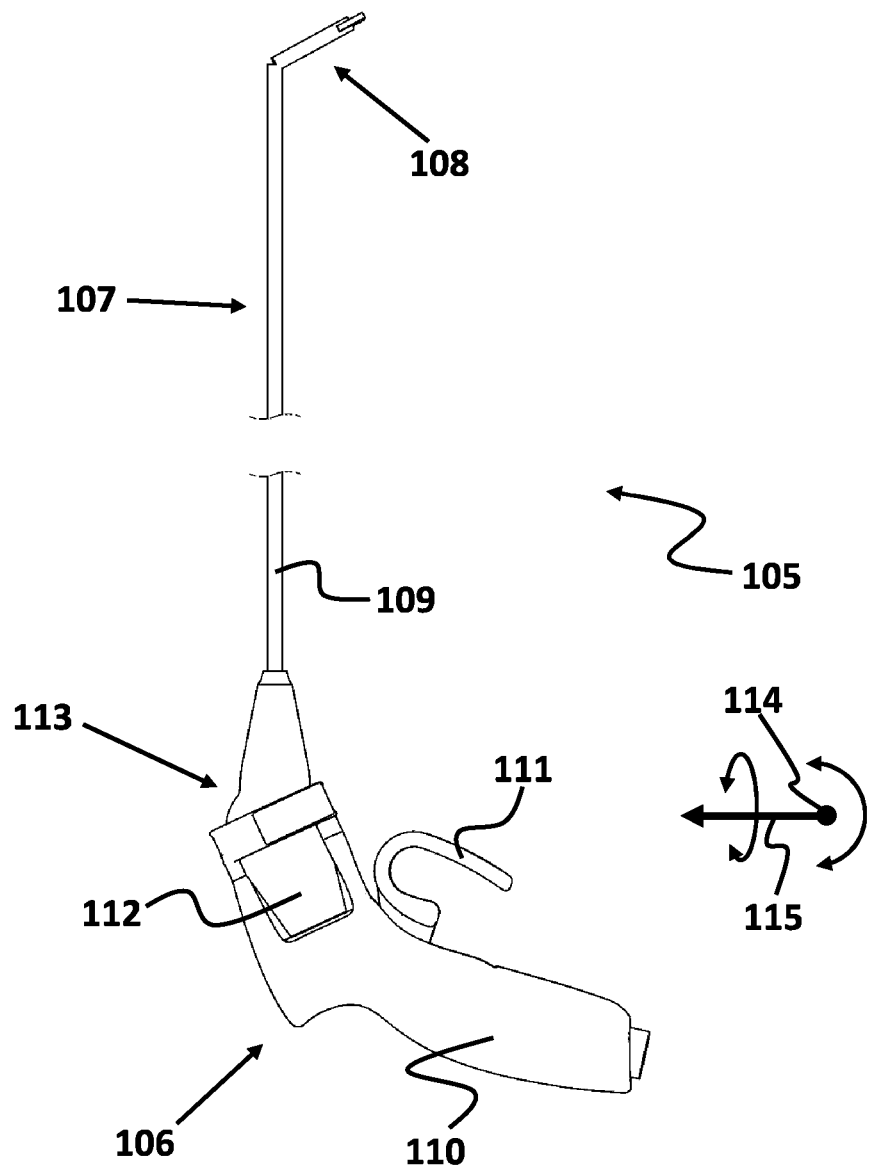
FIG. 1B illustrates an exemplar manual wrist-articulating laparoscopic surgical instrument.
Figure 2A:
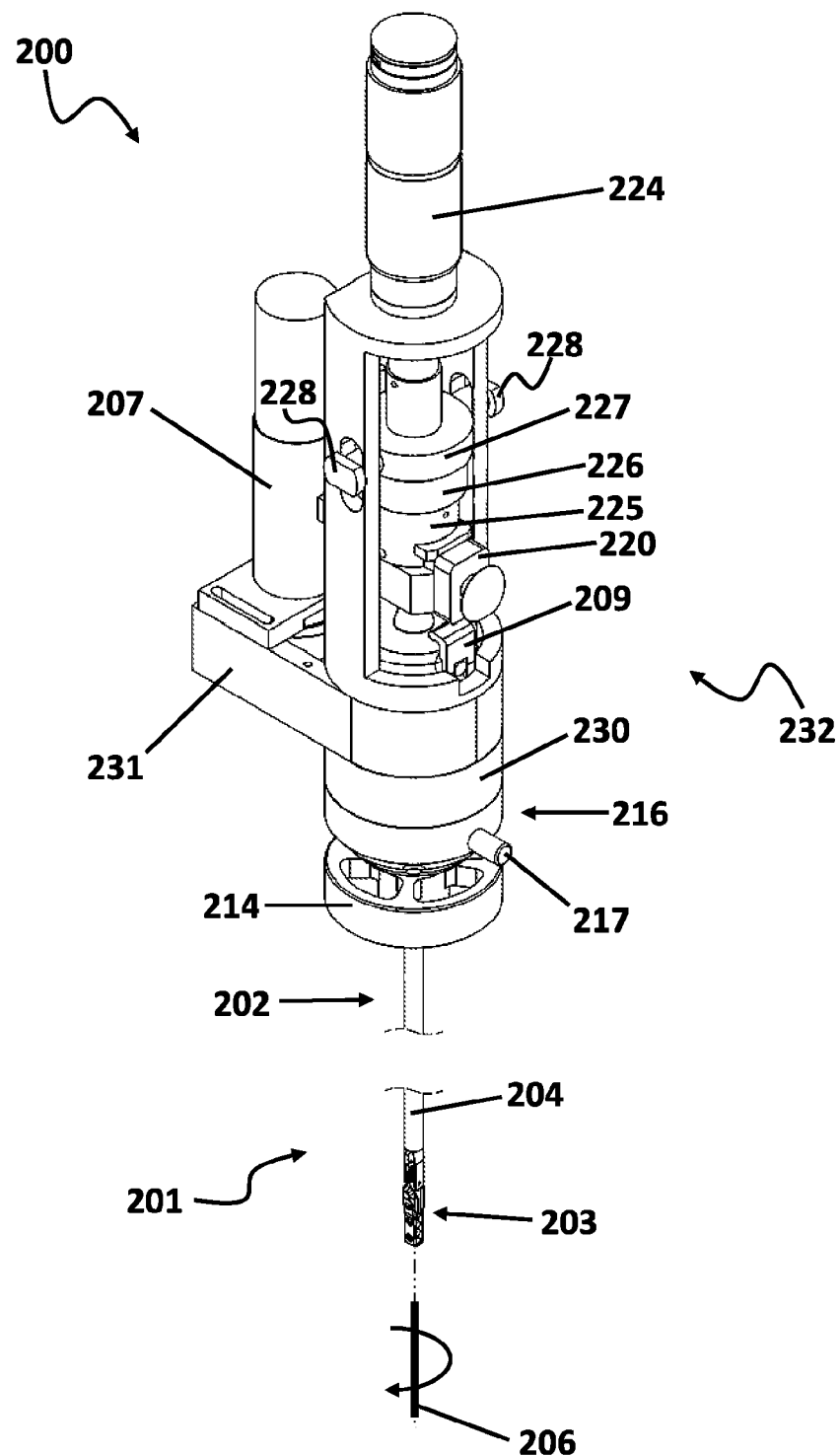
FIG. 2A illustrates a perspective view of a device for connecting and activating simple manual non-articulating laparoscopic surgical instruments on a robotic surgical system, pursuant to aspects of the present application.
Figure 2B:
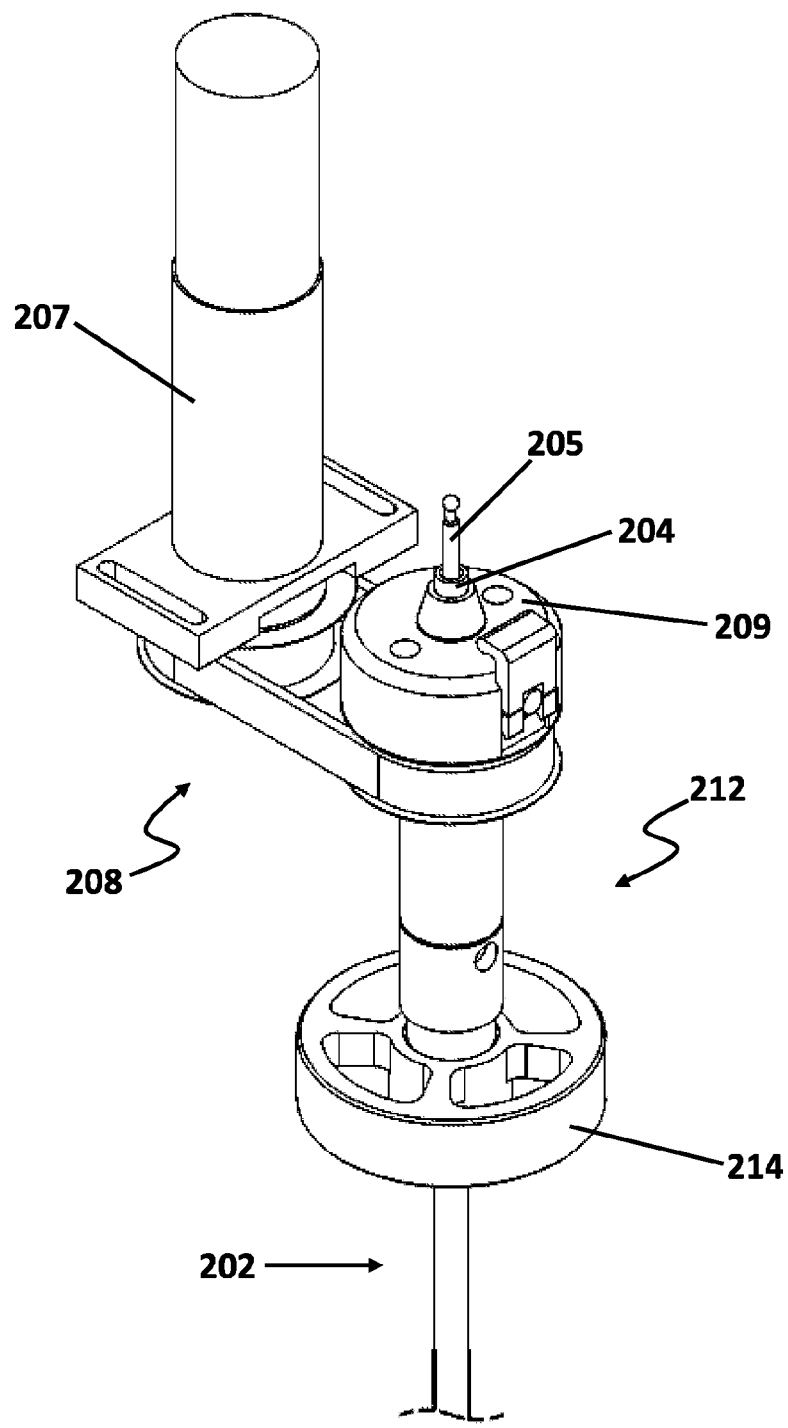
FIG. 2B illustrates a perspective view of a roll actuating mechanism of a device for connecting and activating simple manual non-articulating laparoscopic surgical instruments on a robotic surgical system, as shown in FIG. 2A.
Figure 2C:
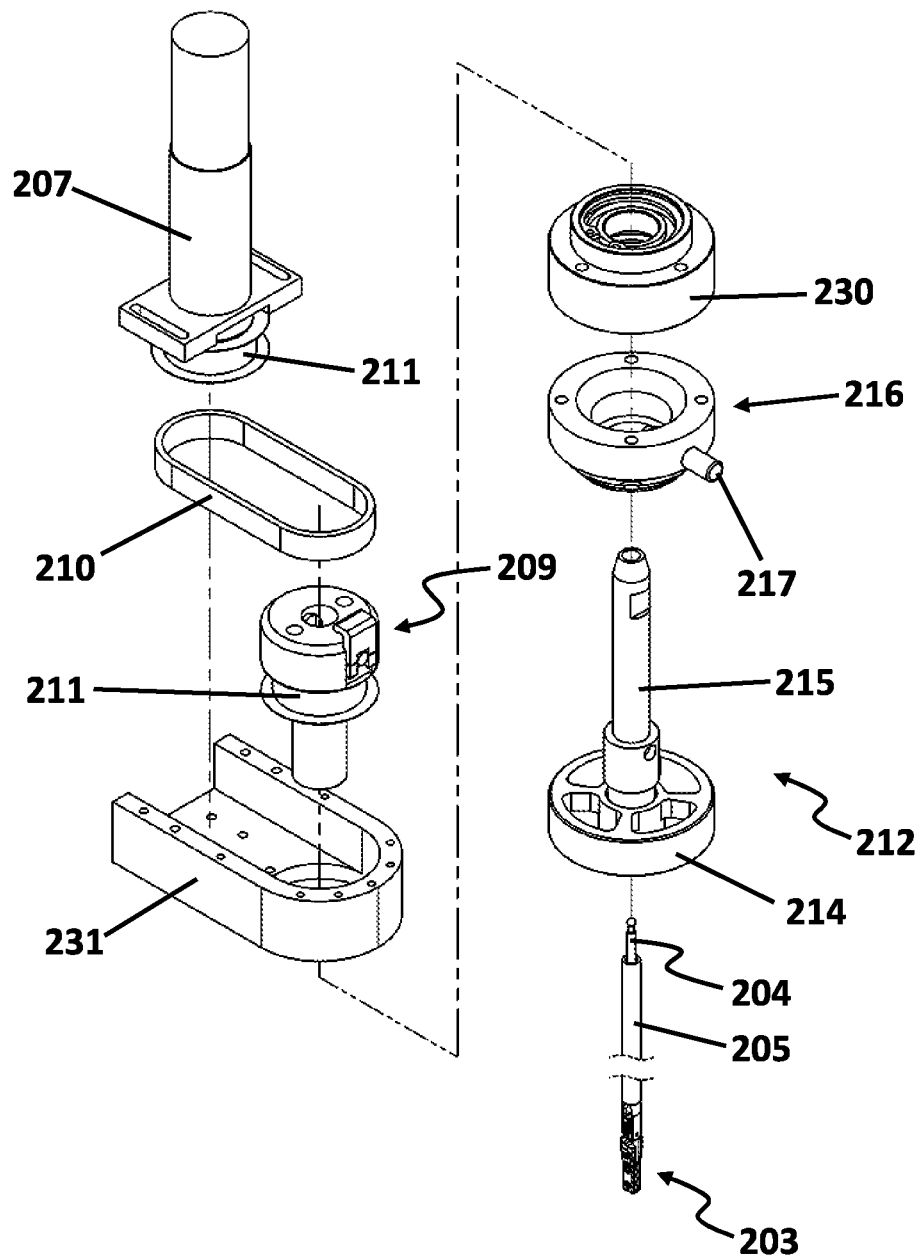
FIG. 2C illustrates an exploded view of a roll actuating mechanism of a device for connecting and activating simple manual non-articulating laparoscopic surgical instruments on a robotic surgical system, as shown in FIG. 2A.
Figure 2D:
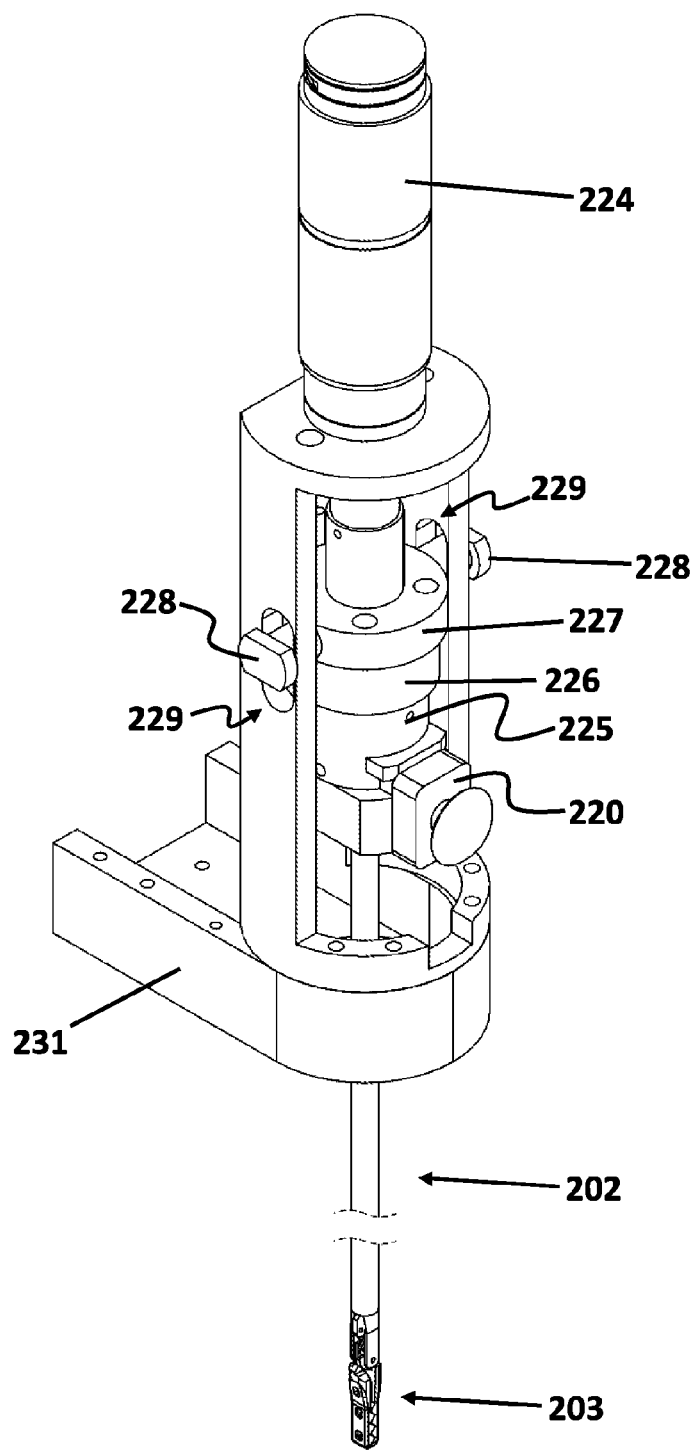
FIG. 2D illustrates a perspective view of a grasp actuating mechanism of a device for connecting and activating simple manual non-articulating laparoscopic surgical instruments on a robotic surgical system, as shown in FIG. 2A.
Figure 2E:
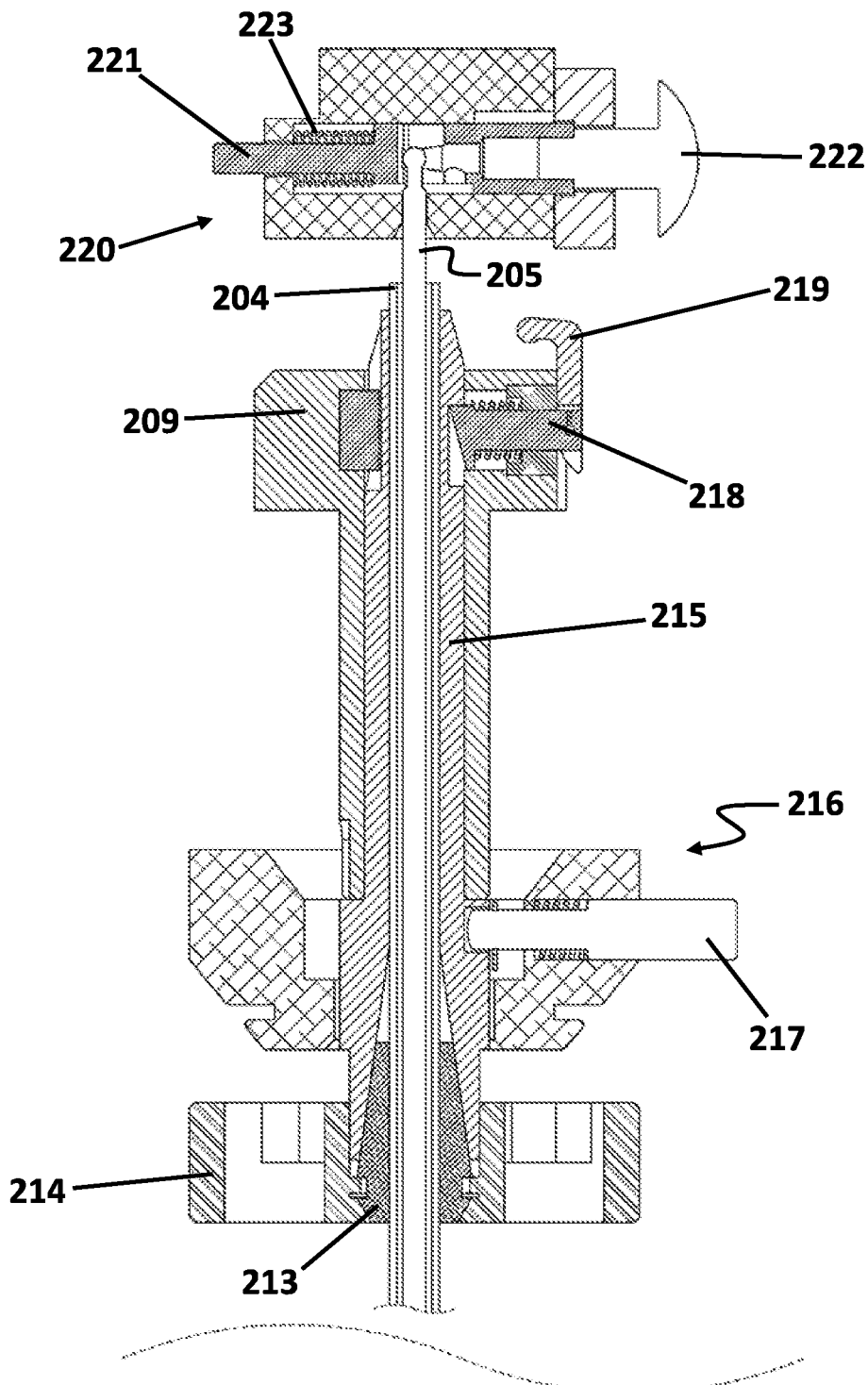
FIG. 2E illustrates a sectional view of a grasp actuating mechanism of a device for connecting and activating simple manual non-articulating laparoscopic surgical instruments on a robotic surgical system, as shown in FIG. 2A.

FIG. 1B illustrates an exemplar manual wrist-articulating laparoscopic surgical instrument 105. The manual wrist-articulating laparoscopic surgical instrument 105 can include: a handle assembly 106, a shaft 107, and an end-effector 108. The handle assembly 106 can be configured with a pistol-type configuration as shown in FIG. 1B or it can utilize a scissor-type configuration, depending on its specific design. The shaft 107 can include a sleeve 109 and an actuating cable (or rod) movable within the sleeve 109 and coupled to the end-effector 108. In FIG. 1B, visibility of the actuating cable (or rod) of the exemplar manual wrist-articulating laparoscopic surgical instrument 105 is obscured by the sleeve 109. In an implementation, though, the general configuration and functionality of the actuating cable (or rod) within the sleeve 109 can be comparable to the actuating cable (or rod) 103 described in reference to FIG. 1A. Referring to FIG. 1B, the shaft 107 can operably interconnect the handle assembly 106 and the end-effector 108. The end-effector 108 can be any effector, such as graspers, cutting forceps, jawed end-effectors, and may be powered for cauterizing. The cauterizing may include electrosurgical cutting and coagulation of tissue. A grasp actuating mechanism can be supported by the handle assembly 106, and depending on the configuration of the handle assembly 106 it can either include a trigger 111, in case of pistol-type configuration or a combination of a stationary handle and a movable handle, in case of scissor-type configuration. The trigger 111 can be coupled to the actuating cable (or rod) within the sleeve 109 in a configuration that linearly pulls the actuating cable (or rod) in an axial linear movement inside the sleeve 109 and thereby activates the grasp DOF of the end-effector 108. The sleeve 109 is configured to allow the actuating cable (or rod) to freely move in response to the trigger 111 motion. The handle assembly 106 can further include a handle grip 110 configured to be grasped by a hand of a surgeon.

In case of scissor-type configuration (not explicitly visible in FIG. 1B), the handle assembly differs from the handle assembly 106 by using, in place of the handle grip 110, a movable handle pivotally linked to a stationary handle, with the actuating cable (or rod) that passes through the sleeve 109 being coupled to the movable handle. Movability of the movable handle about the pivotal link, in combination with being coupled to the actuating cable (or rod) can effectively substitute for the FIG. 1B trigger 111. More specifically, movement of the movable handle about the pivotal link can linearly pull the actuating cable (or rod) in an axial linear movement inside the sleeve 109 and thereby activate the grasp DOF of the end-effector 108.

Referring to FIG. 1B, The handle assembly 106 can further include a roll knob 112, which can be coupled with the shaft 107, such that a roll-rotation of the roll knob 112 leads to a roll-rotation of the shaft 107 about the longitudinal axis of the shaft 107. The roll-rotation of the shaft 107 about the longitudinal axis of the shaft 107 can activate the roll DOF of the end-effector 108, for roll movement of the end-effector 108 about its longitudinal axis.

In a manual wrist-articulating laparoscopic surgical instrument 105, the actuating cable (or rod) that passes through sleeve 109 can include an actuating rod and a plurality of control cables. The actuating rod can pass through a spherical joint (or wrist) 113 and the control cables can be coupled to the spherical joint 113. The control cables can be configured to transfer a pitch- or yaw-rotation of the spherical joint 113 relative to the handle assembly 106, resulting in a corresponding pitch or yaw movement by the end-effector 108. For example, the cables can include pitch cables and yaw cables. The pitch cables can be configured such that a rotation of the spherical joint 113 relative to the handle assembly 106 in a given pitch direction about a pitch axis 114 causes one or more of the pitch cables to pull the end effector 108 in a manner than activates the pitch DOF of the end-effector 108 in a corresponding direction. Similarly, the yaw cables can be configured such that a rotation of the spherical joint 113 relative to the handle assembly 106 about a yaw axis 115 activates the yaw DOF of the end-effector 108 in a corresponding direction.

Exemplar tool adapting devices according to the present application can be configured to hold the manual laparoscopic instruments and activate their grasp, roll, pitch, and yaw DOFs. Exemplar tool adapting devices according to the present application and their tool activating mechanisms can be configured to provide holding and manipulation of manual laparoscopic instruments with or without their handle assembly. Further, the activating mechanism of exemplar tool adapting devices according to the present application can, according to various aspects, be configured to activate the grasp, roll, pitch, and yaw DOFs of the laparoscopic surgical instruments by imitating manipulating movements of a surgeon's hand.

For example, in order to activate the grasp DOF of the end-effector, the tool activating mechanism can include a first actuating mechanism to move the actuating cable (or rod) in a linear axial movement inside the sleeve along the longitudinal axis of the shaft of the instrument. The first actuating mechanism can be configured to either directly engage the actuating cable (or rod) in case of handle-free instruments or engage a grasp control mechanism such as a trigger or a movable handle in case of handled instruments.

In addition, in order to activate the roll DOF of the end-effector, the tool activating mechanism can include a second actuating mechanism, which can be configured to rotate the shaft about the longitudinal axis of the shaft. The second actuating mechanism can be configured to engage the shaft directly and drive a roll-rotation movement of the shaft, thereby activating a corresponding roll rotation of the end-effector about the longitudinal axis of the end-effector.

Additionally, in order to activate the pitch and yaw DOFs of the end-effector, the tool activating mechanism can include a third actuating mechanism, which can be configured to rotate the spherical joint or the wrist of the surgical instrument about pitch and yaw axes, in case of wrist-articulating instruments.

In some implementations, the first actuating mechanism, the second actuating mechanism, and the third actuating mechanism can include servo motors, configured to function as rotational actuators. The tool activating mechanism can be controllable via the robotic surgical arm. The robotic surgical arm can control the movement of the actuators via a controller that controls the drivers of the servo motors.

FIGS. 2A-2E illustrate an exemplar tool adapting device 200 for connecting and manipulating a manual non-articulating laparoscopic surgical instrument 201 on a robotic surgical system. The tools adapting device 200 can include: an attachment interface 231, and a tool activating mechanism 232.

The manual non-articulating laparoscopic surgical instrument 201, which is held and manipulated by the tool adapting device 200, can include a shaft 202 and an end-effector 203. The shaft 202 can include a sleeve 204 and an actuating cable (or rod) 205 (visible in FIGS. 2B and 2C) movable inside the sleeve 204. The surgical instrument 201 may have two DOFs, for example, a roll DOF and a grasp DOF.

The activating mechanism 232 of the tool adapting device 200 can activate the roll DOF by a rotational actuation of the shaft 202 about a longitudinal axis 206 of the shaft. The roll-rotation of the shaft 202 about the longitudinal axis 206 effects simultaneous roll-rotations of the sleeve 204 and the actuating cable (or rod) 205 inside the sleeve 204. The roll-rotation of the shaft 202 about the longitudinal axis 206 thereby induces a roll-rotation movement of the end-effector 203 about the longitudinal axis 206. The grasp DOF may be activated by a linear actuation of the actuating cable (or rod) 205 relative to the sleeve 204, along the longitudinal axis 206 of the shaft. The linear axial movement of the actuating cable (or rod) 205 inside the sleeve 204 results in activation of grasp DOF of the end-effector 203. The end-effector 203 can be any effector, such as graspers, cutting forceps, jawed end-effectors, or may be powered for cauterizing.

According to the implementation shown in FIGS. 2A-2E, the tool activating mechanism 232 can include a rotational actuator 207, which can be used for activating the roll DOF of the end-effector 203. The rotational actuator 207 may be connected by a belt-and-pulley mechanism 208 to an intermediate holding member 209. The belt-and-pulley mechanism 208 can include a belt 210 and two pulleys 211 and can transfer the roll-rotation movement driven by the rotational actuator 207 to the intermediate holding member 209. The intermediate holding member 209 can be configured to hold and facilitate roll-rotation movement of a sterilizable shaft holding unit 212. The sterilizable shaft holding unit 212 can be configured to hold and support the shaft 202.

It may become apparent to a person skilled in the art, upon reading this disclosure, that there can be other implementations of coupling the rotational actuation mechanism to the shaft 202. For example, the rotational actuation mechanism can be coupled to the shaft 202 via gear mechanisms, chain-wheel mechanism, or belt-and-pulley mechanisms. According to some implementations, the belt-and-pulley mechanism 208 can be a timing belt-and-pulley mechanism.

According to one implementation, the sterilizable shaft holding unit 212 can include: a collet 213 (labeled in FIG. 2E), a collet nut 214, a shaft guiding member 215, and a fixing mechanism 216. The shaft 202 can be inserted into the sterilizable shaft holding unit 212. The collet 213 can be used to grip the sleeve 204 and the collet nut 214 can be used to tighten the collet 213 and the shaft guiding member 215 around the sleeve 204 in order to enable a tight grip of the sleeve 204 inside the sterilizable shaft holding unit 212. The fixing mechanism 216 can include a spring-loaded pin 217 to prevent the shaft guiding member 215 from linear movements along the longitudinal axis 206; therefore, the sleeve 204 can only have roll-rotational movements. In one implementation, a bearing 230 can be utilized to facilitate the roll-rotation of the sterilizable shaft holding unit 212.

The intermediate holding member 209 can include a spring-loaded pin 218 and a detachment lever 219. The sterilizable shaft holding unit 212 can be inserted inside the intermediate holding member 209. The spring-loaded pin 218 can hold the sterilizable shaft holding unit 212 inside the intermediate holding member 209. The intermediate holding member 209, which can be coupled to the rotational actuator 207 by the belt-and-pulley mechanism 208, can be configured to facilitate the roll-rotation of the sterilizable shaft holding unit 212, which can activate the roll DOF of the end-effector 203.

In some implementations, in order to detach the sterilizable shaft holding unit 212 from the intermediate holding member 209, the detachment lever 219 may be pulled to pull back the spring-loaded pin 218 and release the sterilizable shaft holding unit 212. It should be known that in medical and surgical applications all structures and surfaces in contact with the surgical tool must be sterilized. Therefore an easy to release holding unit can be useful.

An insert holding member 220 (labeled in FIGS. 2A, 2D and 2E) can be used to hold the actuating cable (or rod) 205 of the surgical instrument 201. The insert holding member 220 can be configured to hold the actuating cable (or rod) 205 in a way that the actuating cable (or rod) 205 can freely roll about the longitudinal axis 206 while being held by the insert holding member 220.

In one implementation, the insert holding member 220 can include: an insert holding pin 221, and a release button 222. Once the release button 222 is pushed, the insert holding pin 221, which is a spring-loaded pin is pushed back and the actuating cable (or rod) 205 is released, and once the release button 222 is released, the insert holding pin 221 is pushed back in place by a spring 223 and holds the actuating cable (or rod) 205 inside the insert holding member 220.

According to some implementations, in order to place the actuating cable (or rod) 205 inside the insert holding member 220, a first operation can be a pushing of the release button 222, which causes the insert holding pin 221 to be pushed back, followed by an operation of placing the actuating cable (or rod) 205 inside the insert holding member 220, and then releasing the release button 222. The insert holding pin 221 then jumps back in place and holds the actuating cable (or rod) 205 inside the insert holding member 220.

According to one implementation, the tool activating mechanism 232 can include a linear actuation mechanism, which can be utilized to activate the grasp DOF of the end-effector 203. The linear actuation mechanism can include a rotational actuator 224 coupled with, for example, a ball screw assembly. The ball screw assembly translates the rotational movement of the rotational actuator 224 into a linear movement of the insert holding member 220 along the longitudinal axis 206. The axial movement of the insert holding member 220 is transferred to the actuating cable (or rod) 205 and the sliding linear movement of the actuating cable (or rod) 205 inside the sleeve 204 activates the grasp DOF of the end-effector 203.

According to the implementation shown in FIGS. 2A-2E, a connecting member 225 can be utilized to transfer the linear translational movement of the linear actuation mechanism to the insert holding member 220. The insert holding member 220 can be couple to the connecting member 225. In one implementation, the insert holding member 220 can slide into a slit on the connecting member 225. A force sensor 226 can be attached to the connecting member 225 from one side and to the linear actuation mechanism by a flange 227, from the other side. The force sensor 226 is utilized to measure the grasp force and send a force feedback to the surgeon.

According to one implementation, the flange 227 can be configured to also function as a linear guide. For example, two pins 228 can be attached to the flange 227 from either side. The two pins 228 can move inside two slits 229, which can provide the linear guide function of limiting their movement to a linear axial movement up and down inside the slits 229. This prevents a roll-rotation movement of the ball-screw, which leads to the ball screw having only a translational linear movement along the longitudinal axis 206.

The linear actuation mechanism drives the translational linear movement of the insert holding member 220, which can cause a translational sliding linear movement of the actuating cable (or rod) 205 inside the sleeve 204. The translational sliding linear movement activates the grasp DOF of the end-effector 203. In some implementations, a coagulator can be connected to the insert holding pin 221 to power the end-effector 203 for cauterizing. The cauterizing may include electrosurgical cutting and coagulation of tissue.

In some implementations the insert holding member 220 can be a sterilizable insert holding member. The example configuration of the insert holding member 220 provides for easy detachment from the device 200 by pulling the insert holding member 220 out of the slit of the connecting member 225.

It should be understood that a number of different linear actuating mechanisms may be utilized for activating the grasp DOF, including, for example, ball screw mechanisms, nut screw mechanisms, electromagnetic linear actuators, rack-and-pinion mechanisms, cable mechanisms, electrical, pneumatic or hydraulic jacks, etc.

The attachment interface 231 of the tool adapting device 200 can be utilized for connecting the device to a distal end of an arm of the robotic surgical system. In the implementation shown in FIGS. 2A-2E, the attachment interface 231 also functions as a base, on which the tool activating mechanism 232 is mounted.

FIGS. 3A-3E illustrate an exemplar tool adapting device 300 for connecting and activating a handled wrist-articulating laparoscopic surgical instrument 301 on a robotic surgical system. In an aspect, the tool adapting device 300 can include an attachment interface 335 and a tool activating mechanism 338.

Figure 3A:
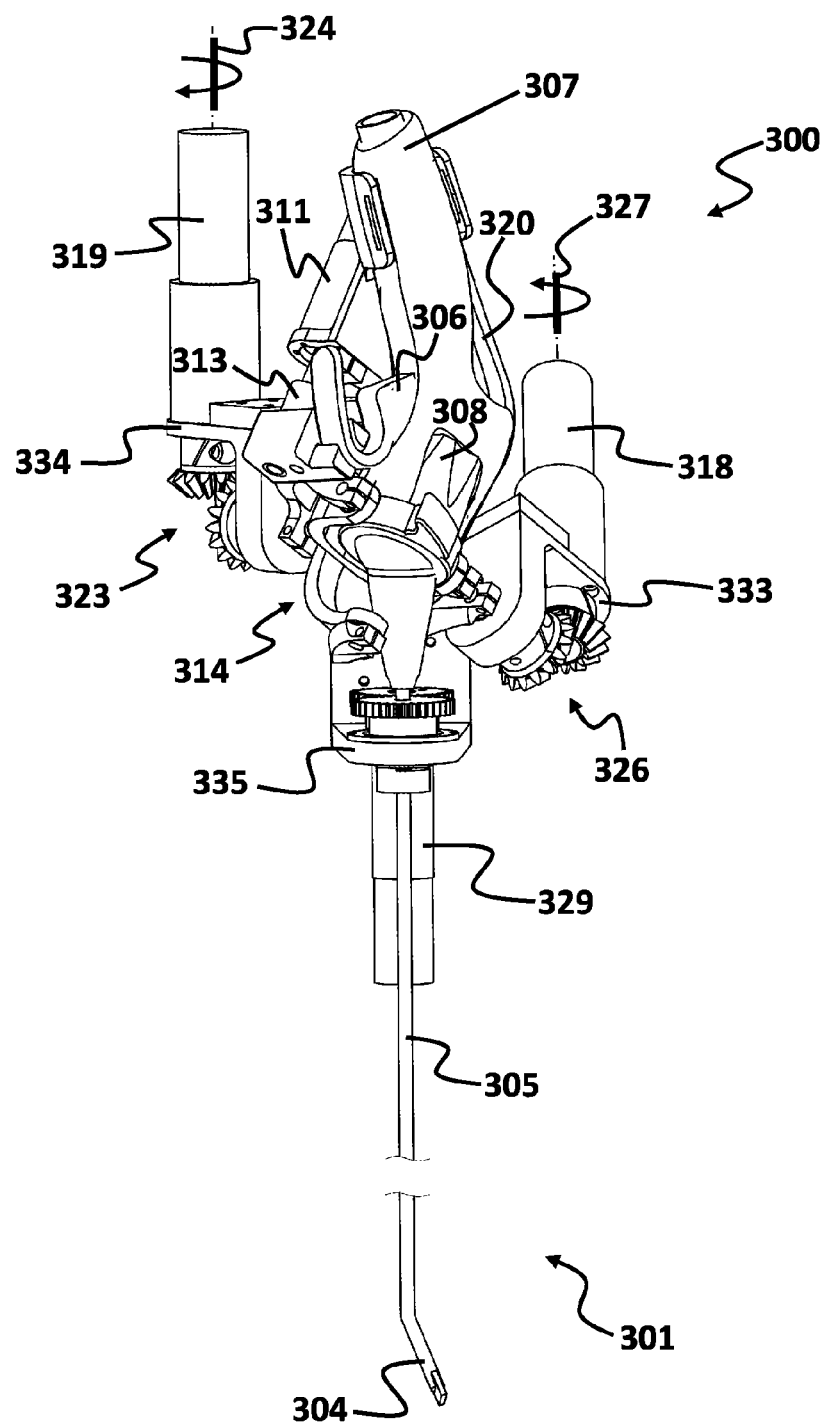
FIG. 3A illustrates a perspective view of a device for connecting and activating manual wrist-articulating laparoscopic surgical instruments on a robotic surgical system, pursuant to the teachings of the present application.

Referring to FIG. 3A, according to this implementation, the handled wrist-articulating laparoscopic surgical instrument 301, which is held and manipulated by the tool adapting device 300, may include a handle assembly 302, a shaft 303, and an end-effector 304. As one non-limiting example practice according to the present application, the handled wrist-articulating laparoscopic surgical instrument 301 can be structured such as, or with similarity to the FIG. 1B exemplar manual wrist-articulating laparoscopic surgical instrument 105. The handle assembly 302 can be configured with a pistol-type configuration. The shaft 303 can include a sleeve 305 and an actuating cable (or rod) (obstructed from view in FIG. 3A) movable within the sleeve 305. The shaft 303 operably interconnects the handle assembly 302 and the end-effector 304. The end-effector 304 can be any effector, such as graspers, cutting forceps, jawed end-effectors, or may be powered for cauterizing. The cauterizing may include electrosurgical cutting and coagulation of tissue. The handle assembly can include a handle grip 307, which can be configured to be grasped by a hand of a surgeon. A handle actuating mechanism supported by the handle assembly 302 can include a trigger 306, and a roll knob 308. As an illustrative, non-limiting example, the trigger 306 and roll knob 308 can have respective functions and configurations such as, or equivalent to, the respective functions and configurations of the FIG. 1B trigger 111 and roll knob 112. The handle assembly 302 can be coupled with the shaft 303 by a spherical joint 309. The trigger 306 can be rotatably coupled to the handle 302, and can be configured to rotate about a pivot point. The trigger 306 can be coupled to the actuating cable (or rod). The actuating cable (or rod) can be configured to operably couple with the end-effector 304, such that displacement of the actuating cable (or rod), e.g., in response to the trigger 306 motion, results in the activation of the grasp DOF of the end-effector 304. Further, the actuating cable (or rod) can be configured such that displacement of the actuating cable (or rod) in response to a pitch- or yaw-rotation of the spherical joint 309 causes activation of the pitch or yaw DOFs of the end-effector 304. The roll knob 308 can be coupled to the actuating cable (or rod). The coupling of the actuating cable (or rod) to the end-effector can provide roll rotation of the end-effector 304 about its longitudinal axis, corresponding to roll-rotation of the actuating cable (or rod) in response to the roll-rotation of the roll knob 308.

In order to activate the grasp DOF in the handled wrist-articulating laparoscopic surgical instruments 301, the tool activating mechanism 338 can include a linear actuation mechanism 310, which can be used to move the actuating cable (or rod). The actuating cable (or rod) can be configured to operably couple the end-effector 304, such that displacement of the actuating cable (or rod) along the longitudinal axis of the sleeve 305 activates the grasp DOF of the end-effector 304.

Figure 3B:
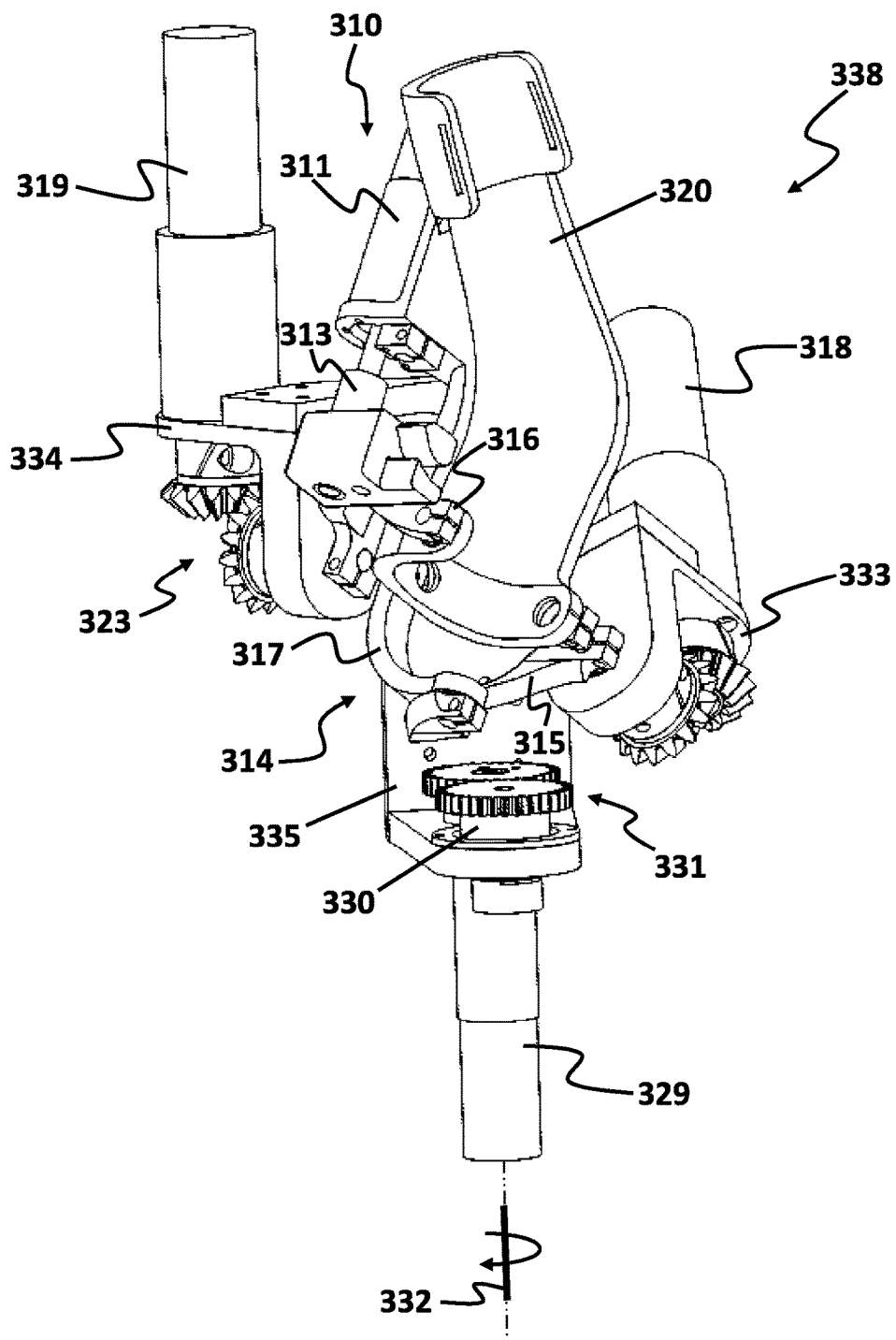
FIG. 3B illustrates a perspective view of a device as shown in FIG. 3A without the manual surgical instrument.
Figure 3C:
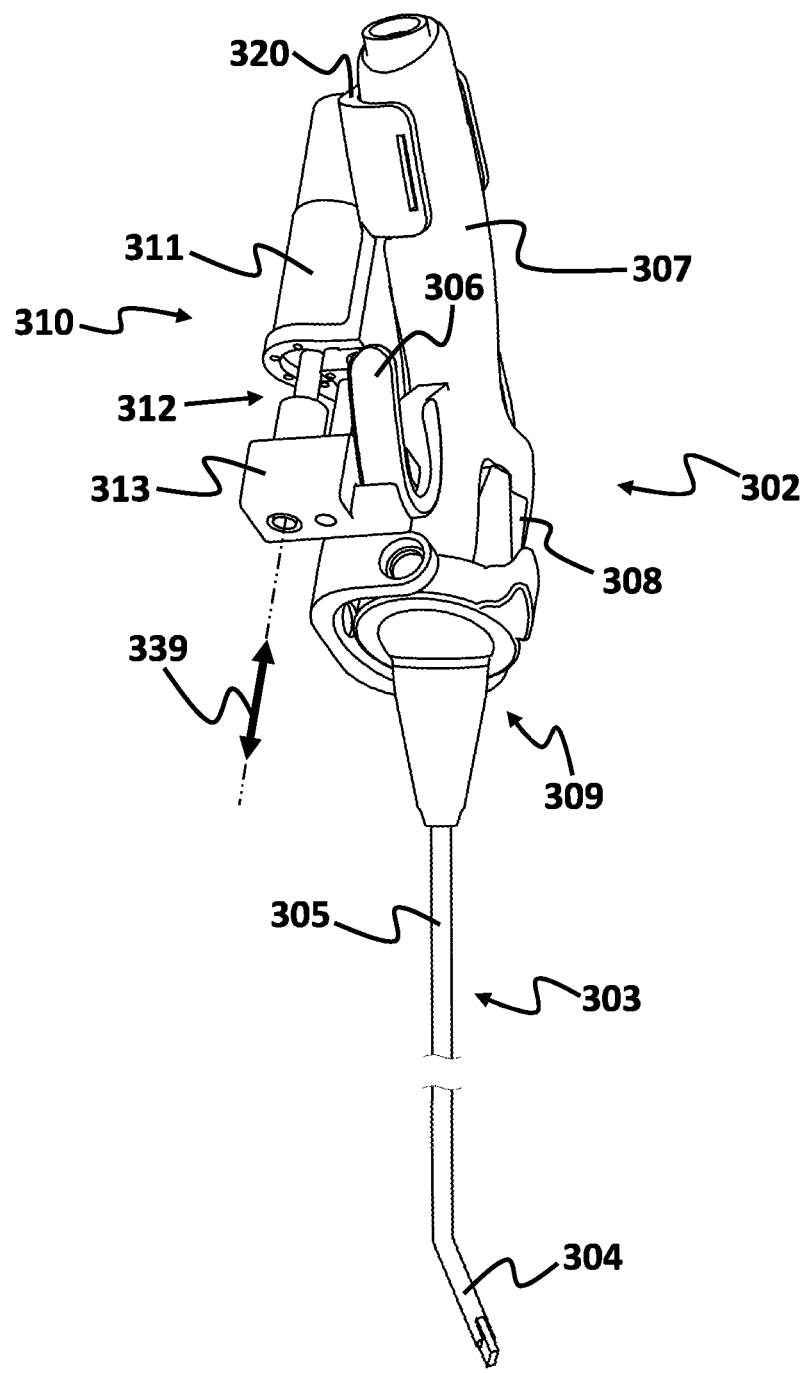
FIG. 3C illustrates a perspective view of a grasp actuating mechanism of a device for connecting and activating manual wrist-articulating laparoscopic surgical instruments on a robotic surgical system, as shown in FIG. 3A.
Figure 3D:
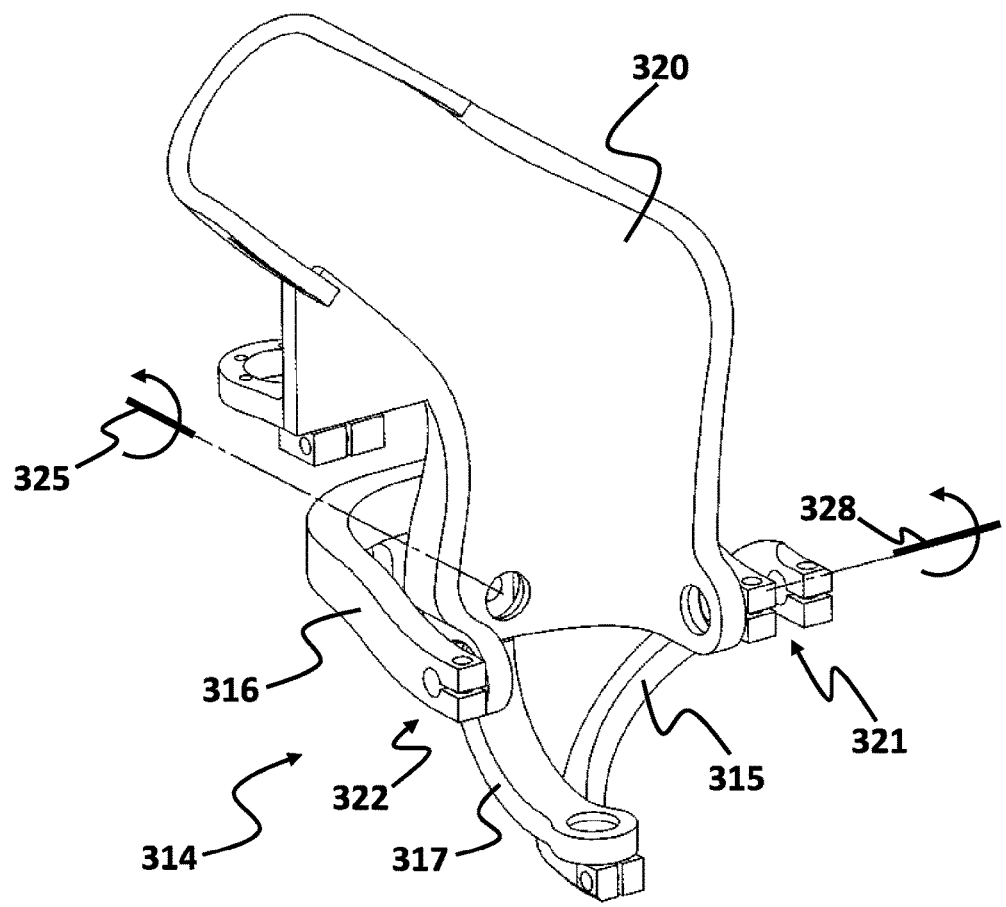
FIG. 3D illustrates a perspective view of a spherical mechanism of a device as shown in FIG. 3A.
Figure 3E:
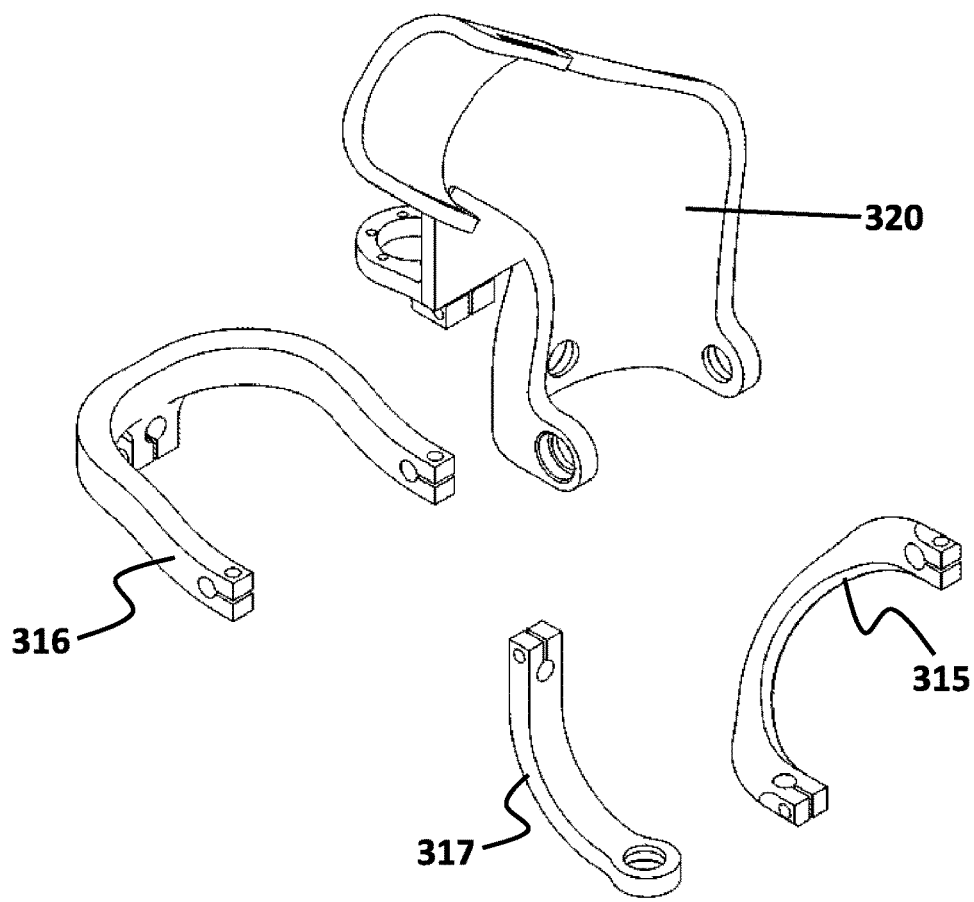
FIG. 3E illustrates an exploded view of a spherical mechanism of a device as shown in FIG. 3A.

In some implementations, the linear actuating mechanism 310, can include a rotational actuator 311 coupled to a ball screw assembly 312 (labeled on FIG. 3C). The ball screw assembly 312 can be configured to translate the rotational movement of the rotational actuator 311 into a linear movement of a mechanical finger 313 along a linear axis 339. The mechanical finger 313 can be configured to grab the trigger 306 and pull the trigger 306 back upon actuation and thereby activate the grasp DOF of the end-effector 304. It will be understood by persons of ordinary skill, upon reading this application, that disclosed features of the mechanical finger 313 and its configuration with the trigger 306, in combination with other disclosed aspects, can provide features including translation and adaptation of robotic movement into actuation of a trigger (e.g., the trigger 111 of the FIG. 1B manual wrist-articulating laparoscopic surgical instrument 105) that was designed for direct manual actuation by a surgeon.

It should be understood that the linear actuating mechanism 310 might include other mechanisms, such as nut screw mechanisms, electromagnetic linear actuators, rack-and-pinion mechanisms, cable mechanisms, electrical, pneumatic or hydraulic jacks, etc.

Manual wrist articulating laparoscopic instruments can have two extra pitch and yaw DOFs in addition to the roll and grasp DOFs. In order to activate the pitch and yaw DOFs, the tool activating mechanism 338 can include an actuating mechanism that can be used to move the handle assembly 302 of the handled wrist-articulating laparoscopic instrument 301 about the yaw- and pitch- axes of the handle assembly 302 relative to the shaft 303. A spherical mechanism 314 with two DOFs coupled with an actuating mechanism can be used to activate the pitch and yaw DOFs of the surgical instrument 301. The spherical mechanism 314 can include three links 315, 316, and 317. The actuating mechanism can include a first actuator 318 and a second actuator 319. As shown in more detail in FIGS. 3D and 3E, the link 315 can be coupled with link 317, the first actuator 318, and a handle holding member 320 at one end and to the link 316 at the other end. The link 316 can be coupled with the handle holding member 320.

The second actuator 319 can be coupled with the link 316. The second actuator 319 can be coupled to the link 316 by a bevel gear mechanism 323. The second actuator 319 drives a rotational movement about a first rotation axis 324, and the bevel gear mechanism 323 translates the rotational movement of the second actuator 319 about the first rotational axis 324 into a rotational movement of the link 316 about a second rotational axis 325. The link 316 can be coupled to the handle holding member 320, for example, by two hinge joints 321 and 322.

The first actuator 318 can be coupled to links 315 and 317, for example, by a bevel gear mechanism 326. The first actuator 318 can drive a rotational movement about a third rotation axis 327, and the bevel gear mechanism 326 can translate the rotational movement of the first actuator 318 about the third rotational axis 327 into a rotational movement of the spherical mechanism 314 about a fourth rotational axis 328. A combination of the rotational movement of the spherical mechanism 314 about axes 325 and 328 can be utilized to rotate the handle holding member 320 about pitch and yaw axes. The handle holding member 320 can be configured to grip the handle assembly 302 of the surgical tool 301. The rotational movement of the handle holding member 320 leads to pitch- and yaw-rotation movements in the handle assembly 302 relative to the shaft 303. Pitch- and yaw-rotation movements in the handle assembly 302 relative to the shaft 303 induces a rotational movement of the spherical joint 309 about pitch and yaw axes, which activates the pitch and yaw DOFs of the surgical tool 301.

It should be understood that the bevel gear mechanism 326 is utilized in this exemplar implementation in order to make the design more compact. The first actuator 318 and the second actuator 319 can be coupled to the spherical mechanism 314 directly, according to other implementations.

Figure 3F:
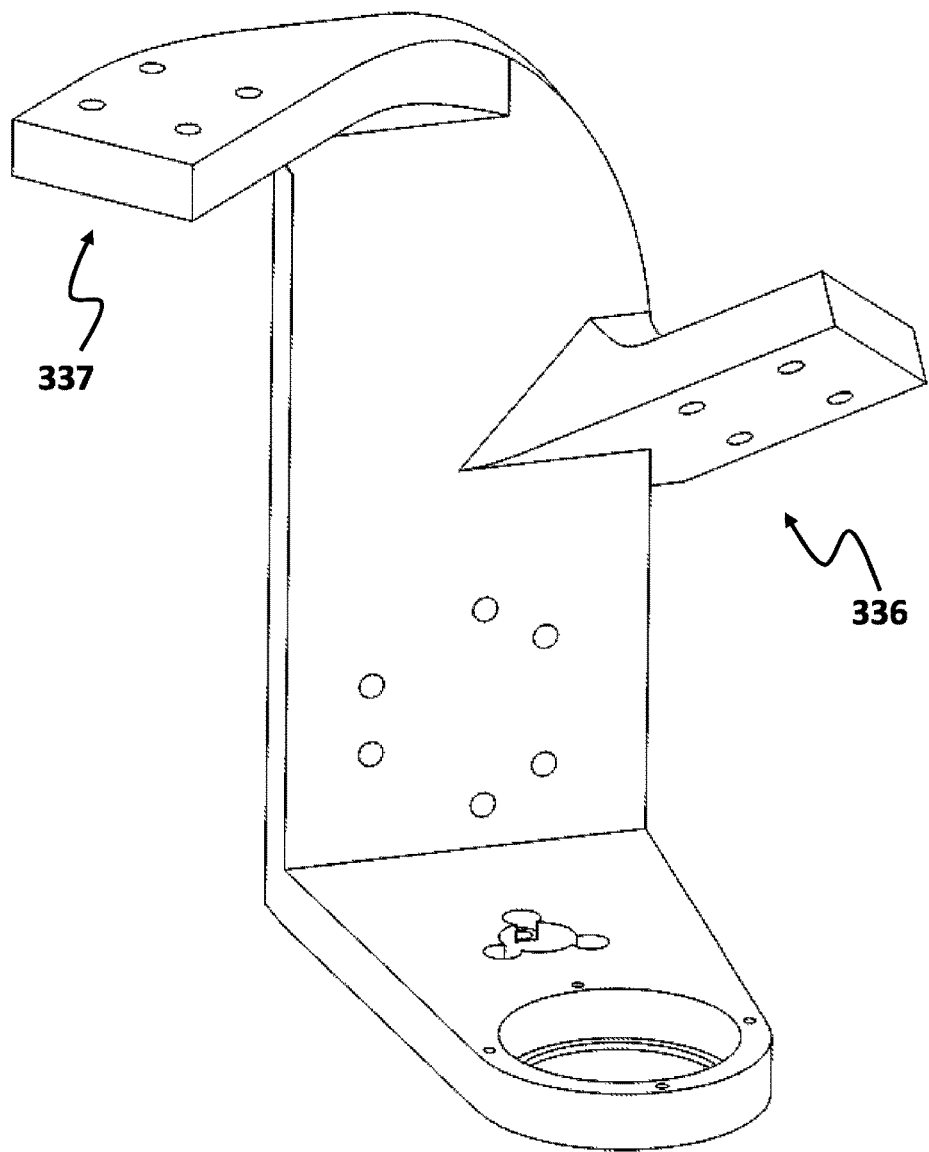
FIG. 3F illustrates a perspective view of an attachment interface of a device as shown in FIG. 3A.
Figure 3G:
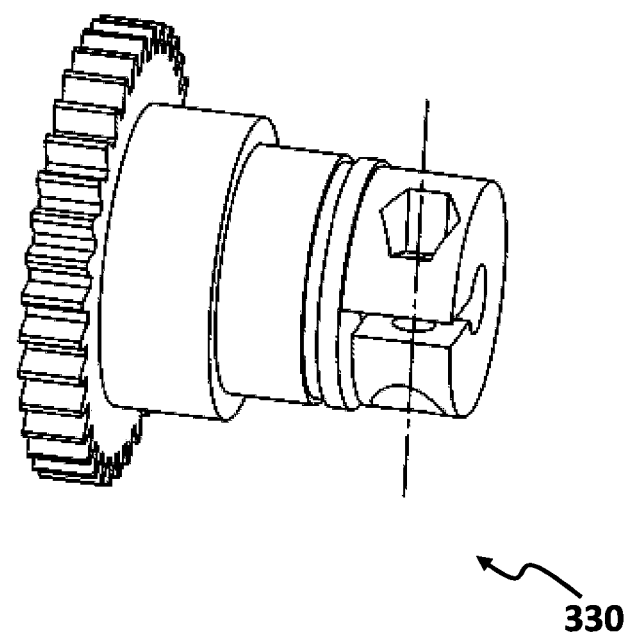
FIG. 3G illustrates a perspective view of a roll gripping member.

The first actuator 318 can be mounted on a first attachment base 336 on the attachment interface 335, for example, by a first mounting member 333. The second actuator 319 can be mounted on a second attachment base 337 on the attachment interface 335, for example, by a second mounting member 334. The attachment interface as shown in FIG. 3F functions to attach the device 300 on a distal end of a robotic surgery arm and is configured to act as a mounting base for the tool activation and tool gripping mechanisms.

The handle holding member 320 can be adaptable to different shapes and designs of the handle grip 307 of the surgical instruments.

As described in reference to FIG. 3A, the handled wrist-articulating laparoscopic surgical instrument 301 can include a roll knob 308. The roll knob 308 may be representative of one or means for manual activation of the roll-rotation DOF of the end-effector 304, when the wrist-articulating laparoscopic surgical instrument 301 is held and used by a surgeon in accordance with its original design. As described above, the exemplar tool adapting device 300 can include a mechanical finger 313 that, in combination with described features for actuating the mechanical finger 313, provides translation and adaptation of a robot operation to the trigger 306. In an aspect, the exemplar tool adapting device 300 can provide translation of a robot operation into the same activation of the roll axis of the sleeve 305 (about the longitudinal axis of the sleeve 305) that was (and still can be) provided by the roll knob 308, but that uses a different roll-activation mechanism, which will now be described. As will be appreciated, the described roll-activation mechanism features provided by the exemplar tool adapting device 300 can leave the roll knob 308 intact. Therefore, the handled wrist-articulating laparoscopic surgical instrument 301 can removed from the exemplar tool adapting device 300 and used again, by a surgeon, for conventional manual surgery. Referring to FIG. 3B, the exemplar tool adapting device 300 can include a roll activating mechanism 338, which can include a roll actuator 329, which can be configured to be rotate about a roll axis 332. The roll actuator 329 can be coupled to a roll gripping member 330, for example, by a gear and pinion mechanism 331. The roll gripping member 330 can be configured to grip the sleeve 305. Accordingly, rotation of the roll actuator 329 about the roll axis 332 is transferred by the gear and pinion mechanism 331 into a rotation of the roll gripping member 330 which, by gripping the sleeve 305, causes roll-rotation of the sleeve 305 about its longitudinal axis. The roll-rotation of the sleeve 305 in turn activates the roll-rotation DOF of the end-effector 304. The roll rotation of the sleeve 305 may induce a roll rotation of the roll knob 308, but this has no operative effect.

According to an implementation, the linear actuating mechanism 310 can be mounted on the handle holding member 320, and therefore, the linear actuating mechanism 310 moves with the handle holding member 320.

FIGS. 4A-4D illustrate an exemplar tool adapting device 400 for connecting and manipulating a handle-free wrist-articulating laparoscopic surgical instrument 401 on a robotic surgical system. According to this implementation, the surgical instrument 401 may include a shaft 402, and an end-effector (not shown). The shaft 402 can include a sleeve 405 and an actuating cable (or rod) 404 movable within the sleeve 403. The actuating cable (or rod) 404 can be operably coupled with the end-effector. The end-effector can be any effector, such as graspers, cutting forceps, jawed end-effectors, or may be powered for cauterizing. The cauterizing may include electrosurgical cutting and coagulation of tissue.

In order to activate the grasp DOF in the handle-free wrist-articulating laparoscopic surgical instrument 401, the tool activating mechanism can include a first linear actuation mechanism 406 that can be used to move the actuating cable (or rod) 404 in an axial sliding movement. The actuating cable (or rod) 404 can be configured to operably couple the end-effector, such that the axial sliding movement of the actuating cable (or rod) 404 inside the sleeve 405 activates the grasp DOF of the end-effector. The first linear actuating mechanism 406 can include: a first rotational actuator 407, a first ball screw assembly 408 coupled to the first linear actuating mechanism 406, a first movable member 409 connected to the ball screw assembly 408 and mounted on a rail-and-wagon assembly 410. The first ball screw assembly 408 can be configured to translate the rotational movement of the first rotational actuator 407 into a linear movement of the first movable member 409. The first movable member 409 can be configured to grip the actuating cable (or rod) 404 and facilitate its linear movement along a sliding axis 411. The rail-and-wagon assembly 410, on which the first movable member 409 is mounted, can function as a linear guide for the linear movement of the first movable member 409 along the axis 411.

According to one implementation, the actuating cable (or rod) 404 can be extended by a cable extension assembly. The cable extension assembly can include a cable connecting member 412, a cable guiding member 413, an extension cable 414 and a supporting member 415.

The tool activating mechanism can include a parallel actuating mechanism (FIG. 4C) for activating the pitch and yaw DOFs of the end-effector. The parallel actuating mechanism can include: a movable platform 418, a fixed platform 419, a second linear actuating mechanism 420, and a third linear actuating mechanism 421. The second linear actuating mechanism 420 can be coupled to the movable platform 418 from one side using a connecting rod 425 and a spherical joint 424 and to the fixed platform 419 using a universal joint 428 from the other side. The third linear actuating mechanism 421 can be coupled to the movable platform 418 from one side using a connecting rod 427 and a spherical joint 426 and to the fixed platform 419 using a universal joint 429 from the other side. The second linear actuating mechanism 420 and the third linear actuating mechanism 421 can be configured to drive pitch- and yaw-rotation of the movable platform 418 about a first universal joint 422. The movable platform 418 can be connected to the fixed platform 419, for example, by a connecting rod 423 and the first universal joint 422. The fixed platform 419 can be attached to the attachment interface of the tool adapting device 400. The movable platform 418 can be rotated about a pitch axis 430 and a yaw axis 431 parallel to pitch and yaw axes of the first universal joint 422. The movable platform 418 can be coupled with the surgical instrument 421 using a spherical joint 432, which allows the cable guiding member 413 to slide through the joint 432. The parallel mechanism functions to translate the linear movements driven by the first and the second actuating mechanisms 420 and 421 into a pitch- and yaw-rotation of the movable platform 419, which in turn moves the cable guiding member 413 and thereby turns the wrist joint 417 of the surgical tool 401 about the pitch and the yaw axes and activates the pitch and yaw DOFs of the end-effector.

Figure 4A:
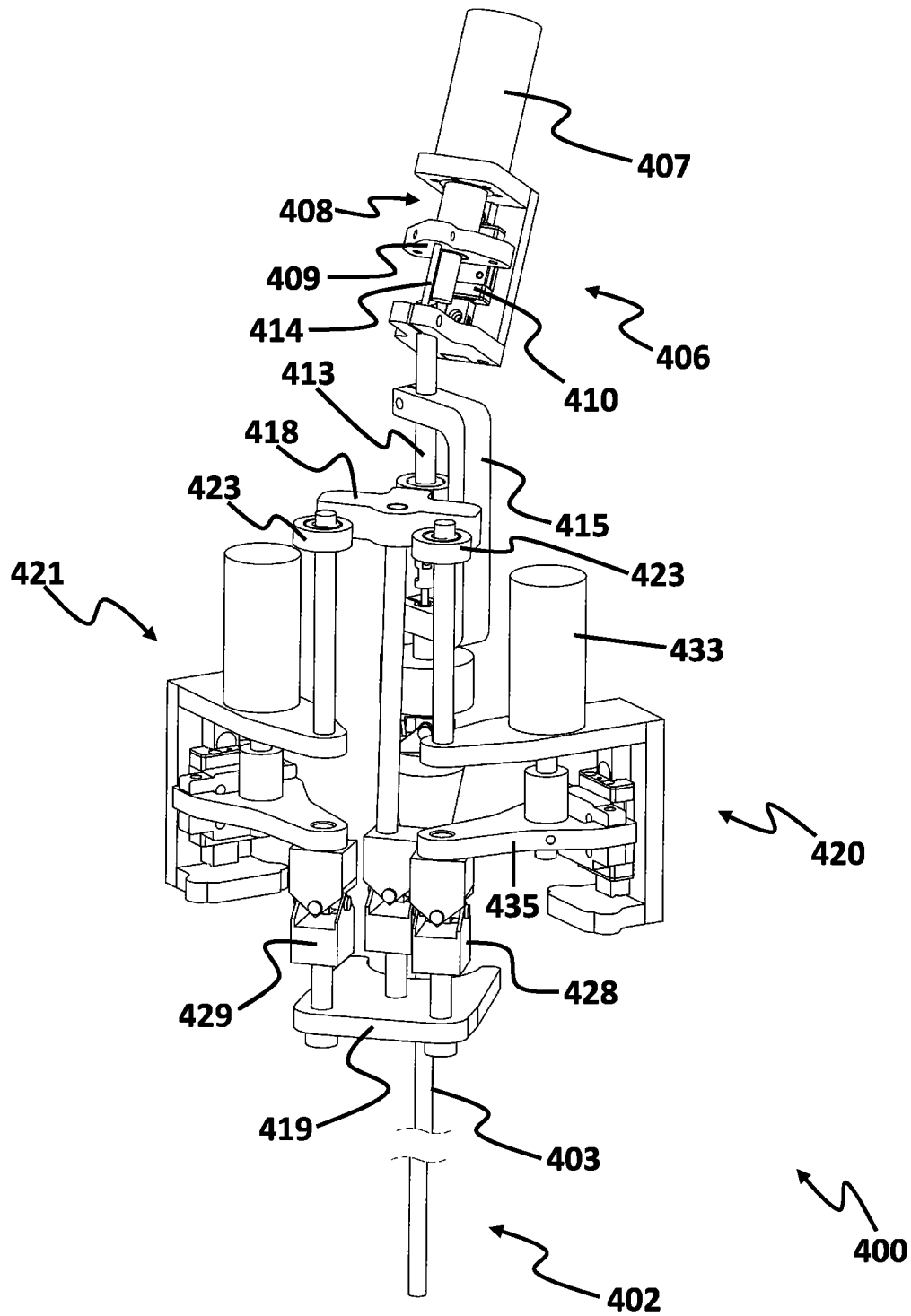
FIG. 4A illustrate a perspective view of a device for connecting and activating manual handle-free wrist-articulating laparoscopic surgical instruments on a robotic surgical system, pursuant to the teachings of the present application.
Figure 4B:
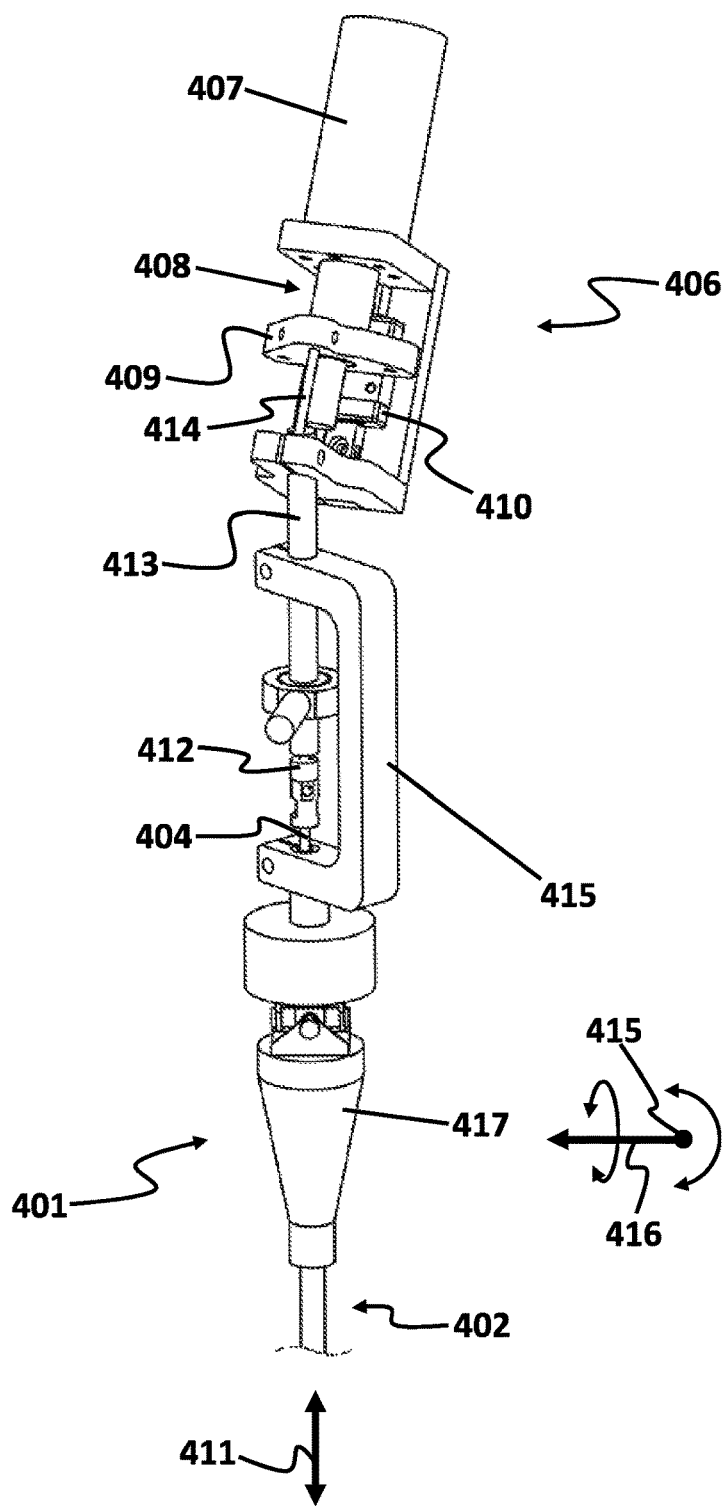
FIG. 4B illustrates a perspective view of a grasp actuating mechanism of a device for connecting and activating manual handle-free wrist-articulating laparoscopic surgical instruments on a robotic surgical system, as shown in FIG. 4A.
Figure 4C:
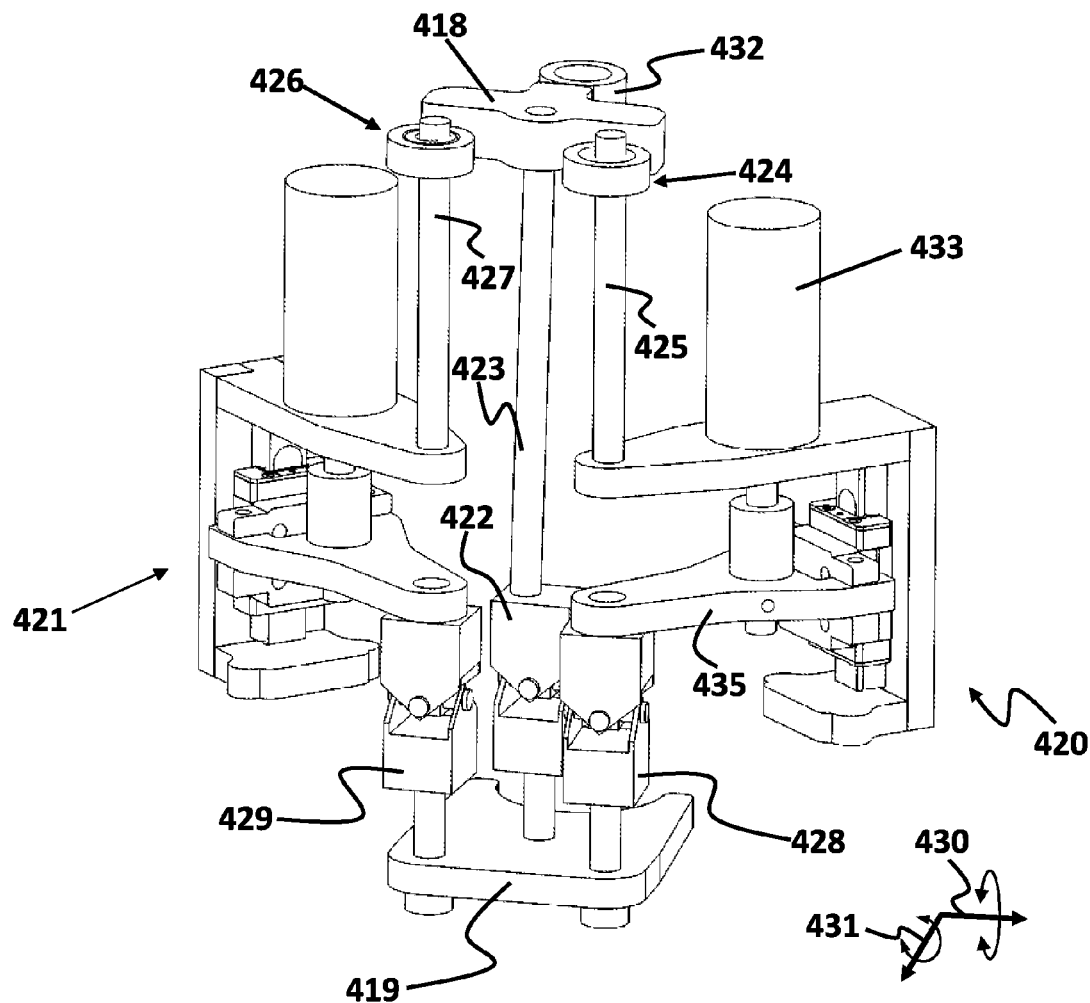
FIG. 4C illustrates a perspective view of a parallel mechanism of a device as shown in FIG. 4A.
Figure 4D:
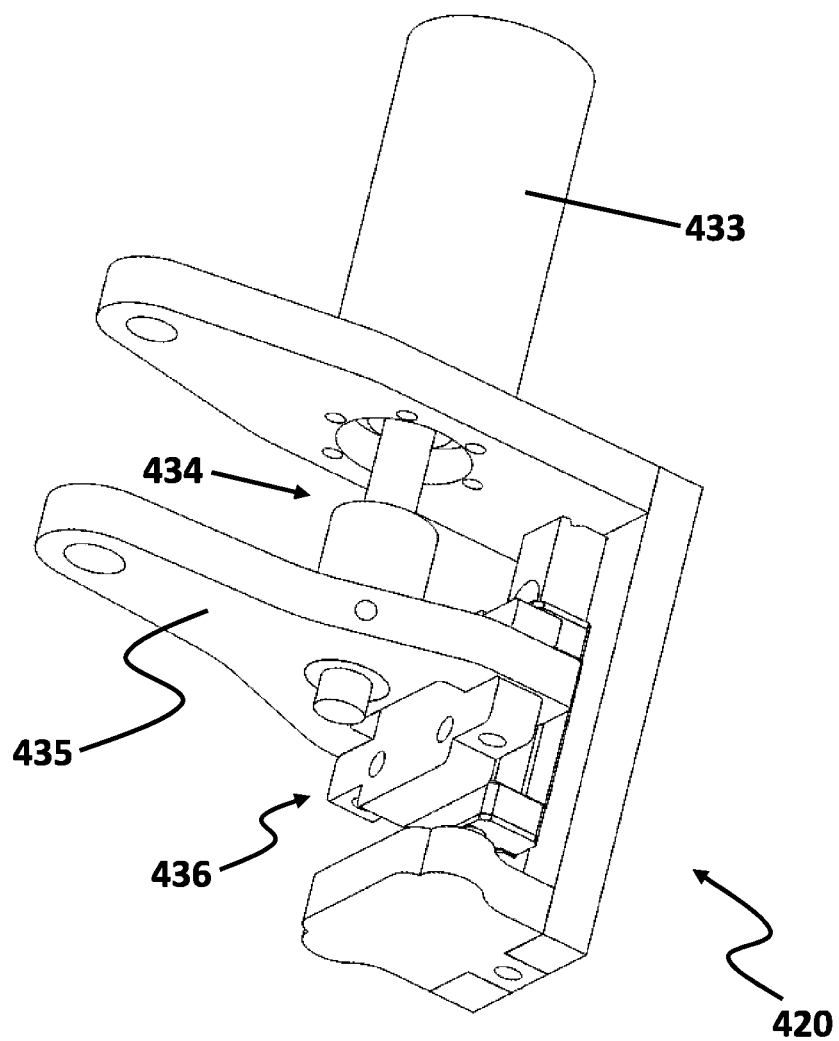
FIG. 4D illustrates a second linear actuating mechanism of the parallel mechanism of a device shown in FIG. 4A.

Referring to FIGS. 4C and 4D, the second linear actuating mechanism can include: a rotational actuator 433, a ball screw assembly 434, a moving member 435, and a rail-and-wagon assembly 436. The ball screw assembly 434 can be coupled with the rotational actuator 433 and to the moving member 435 and functions to translate the rotational movement driven by the rotational actuator 433 into the linear movement of the moving member 435. The moving member 435 can be mounted on the rail-and-wagon assembly 436, and the rail-and-wagon assembly 436 can be configured to function as a linear guide for the moving member 435. The moving member 435 can be coupled with the fixed platform 419 with the universal joint 428. The third linear actuating mechanism 421 can have a similar configuration as the second linear actuating mechanism 420.

According to the implementations described herein, the tool adapting device of the present disclosure can be utilized to hold and manipulate manual laparoscopic surgical instrument with different configurations, such as non-articulating laparoscopic instruments or wrist-articulating laparoscopic instruments with or without a handle assembly.

In another aspect, the present disclosure describes a method for adapting manual laparoscopic instruments to a distal end of a robotic surgery arm. The method includes the steps of: attaching a tool adapting device on the distal end of the robotic surgery arm; and placing a manual laparoscopic surgical tool inside the tool adapting device, where the tool adapting device activates the degrees of freedom of the manual laparoscopic surgical instrument to manipulate a tissue under surgery.

The tool adapting device, as described in this application, may be utilized to reduce the maintenance costs of robotic tele-surgery systems by enabling replacement of the surgical instruments and other single-use or limited-use components and appliances at the distal end of the surgery arm with no need for extensive trainings. More importantly, the present application describes designs that may reduce the operating costs of the robotic tele-surgery systems by making them capable of working with conventional manual laparoscopic and endoscopic surgical instruments.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirements of Sections 101, 102, or 105 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations for the purpose of streamlining the disclosure. This method of disclosure is not to be interpreted as reflecting an intention that the claimed implementations require more features than are expressly recited in each claim. Rather, as the following claims reflect, inventive subject matter lies in less than all features of a single disclosed implementation. Thus the following claims are hereby incorporated into the Detailed Description, with each claim standing on its own as a separately claimed subject matter.

What is claimed is:

1. A tool adapting device for adapting manual surgical instruments for robotic surgery applications, the device comprising:
   an attachment interface configured for connecting the tool adapting device to a distal end of a robotic surgery arm; and
   a tool activating mechanism configured for holding a manual surgical instrument having a wrist joint, the wrist joint providing the manual surgical instrument with a pitch degree of freedom and a yaw degree of freedom, the tool activating mechanism including a first actuating mechanism coupled with a spherical mechanism, the spherical mechanism being attached to a handle of the manual surgery instrument, the first actuating mechanism being configured to rotate the handle of the manual surgery instrument about the pitch and yaw axes relative to a sleeve of the manual surgical instrument via the spherical mechanism.

2. The device according to claim 1, wherein the manual surgical instrument includes handled wrist-articulating instruments.

3. The device according to claim 1, wherein the degrees of freedom of the manual surgical instrument include grasp and roll.

4. The device according to claim 3, wherein the sleeve of the manual surgical instrument is rotatable along a longitudinal axis and a distal end, and an end-effector at the distal end of the rotatable sleeve, and with an actuating cable movable inside the sleeve and coupled at one end to the effector, and wherein the tool activating mechanism further comprises:
   a second actuating mechanism, configured for activating the grasp degree of freedom of the manual surgical instrument, wherein the second actuating mechanism is configured to move the actuating cable of the manual surgical instrument in a linear axial movement inside the sleeve, along the longitudinal axis of the sleeve, thereby activating the grasp degree of freedom of the end-effector.

5. The device according to claim 4, wherein the second actuating mechanism comprises:
   a linear actuating mechanism coupled with the actuating cable of the manual surgical instrument, and configured to move the actuating cable of the manual surgical instrument in a linear axial movement inside the sleeve along a longitudinal axis of the sleeve, thereby activating the grasp degree of freedom of the end-effector.

6. The device according to claim 5, wherein the linear actuating mechanism is selected from the group consisting of ball screw mechanisms, nut screw mechanisms, electromagnetic linear actuators, rack-and-pinion mechanisms, cable mechanisms, electrical jacks, pneumatic and hydraulic jacks.

7. The device according to claim 5, wherein the linear actuating mechanism includes a rotational actuator coupled with a ball screw assembly.

8. The device according to claim 4, further comprising a third actuating mechanism, the third actuating mechanism being configured for activating the roll degree of freedom of the manual surgical instrument, wherein the third actuating mechanism is configured to rotate the sleeve about the longitudinal axis of the sleeve, thereby activating the roll degree of freedom of the end-effector.

9. The device according to claim 8, wherein the third actuating mechanism comprises:
   a rotational actuating mechanism coupled with the sleeve of the manual surgical instrument, the rotational actuating mechanism being configured to rotate the sleeve about the longitudinal axis of the sleeve, thereby activating the roll degree of freedom of the end-effector.

10. The device according to claim 9, wherein the rotational actuating mechanism is coupled with the sleeve of the surgical instrument via a coupling mechanism, wherein the coupling mechanism is selected from the group consisting of gear mechanisms, chain-wheel mechanism, and belt-and-pulley mechanisms.

11. The device according to claim 4, wherein the tool activating mechanism further comprises a force sensor configured to send a grasp force feedback to the surgeon.

12. The device according to claim 1, wherein the first actuating mechanism includes two rotational actuators, wherein one of the two rotational actuators is configured to rotate the handle of the manual surgery instrument about the pitch axis and the other of the two rotational actuators is configured to rotate the handle of the manual surgery instrument about the yaw axis.

13. A tool adapting device for adapting manual surgical instruments for robotic surgery applications, the device comprising:
   an attachment interface configured for connecting the tool adapting device to a distal end of a robotic surgery arm; and
   a tool activating mechanism configured for holding a manual surgical instrument having a wrist joint, the wrist joint providing the manual surgical instrument with a pitch degree of freedom and a yaw degree of freedom, the tool activating mechanism including a first actuating mechanism coupled with the wrist joint, the first actuating mechanism being configured to rotate the wrist joint of the manual surgery instrument about the pitch and yaw axes relative to a sleeve of the manual surgical instrument.

14. The device according to claim 13, wherein the first actuating mechanism includes two rotational actuators, one being configured to rotate the wrist joint of the manual surgery instrument about the pitch axis, and the other being configured to rotate the wrist joint of the manual surgery instrument about the yaw axis.

* * * * *